(12) United States Patent
Johnson

(10) Patent No.: US 11,357,479 B2
(45) Date of Patent: Jun. 14, 2022

(54) METHOD FOR MEASURING BEHIND THE IRIS AFTER LOCATING THE SCLERAL SPUR

(71) Applicant: ArcScan, Inc., Golden, CO (US)

(72) Inventor: Linda Johnson, Boulder, CO (US)

(73) Assignee: ArcScan, Inc., Golden, CO (US)

( * ) Notice: Subject to any disclaimer, the term of this patent is extended or adjusted under 35 U.S.C. 154(b) by 567 days.

(21) Appl. No.: 16/422,182

(22) Filed: May 24, 2019

(65) Prior Publication Data
US 2020/0015789 A1 Jan. 16, 2020

Related U.S. Application Data

(60) Provisional application No. 62/676,175, filed on May 24, 2018.

(51) Int. Cl.
| | | |
|---|---|---|
| *A61B 8/08* | (2006.01) | |
| *A61B 3/00* | (2006.01) | |
| *A61B 3/117* | (2006.01) | |
| *A61B 8/10* | (2006.01) | |

(52) U.S. Cl.
CPC .......... *A61B 8/5223* (2013.01); *A61B 3/0083* (2013.01); *A61B 3/117* (2013.01); *A61B 8/10* (2013.01)

(58) Field of Classification Search
CPC ....... A61B 8/5223; A61B 5/10; A61B 3/0083; A61B 3/117; G16H 50/30
See application file for complete search history.

(56) References Cited

U.S. PATENT DOCUMENTS

| | | |
|---|---|---|
| 4,245,250 A | 1/1981 | Tiemann |
| 4,817,432 A | 4/1989 | Wallace et al. |
| 5,029,587 A | 7/1991 | Baba et al. |
| 5,293,871 A | 3/1994 | Reinstein et al. |
| 5,331,962 A | 7/1994 | Coleman et al. |
| 6,315,727 B1 | 11/2001 | Coleman et al. |
| 6,491,637 B2 | 12/2002 | Foster et al. |

(Continued)

OTHER PUBLICATIONS

Coleman et al., "Ultrasonography of the Eye and Orbit," Second Edition, published by Lippincott Williams & Wilkins, 2006, 205 pages, uploaded in 4 parts.

(Continued)

*Primary Examiner* — Peter Luong
(74) *Attorney, Agent, or Firm* — Sheridan Ross P.C.

(57) ABSTRACT

A method is disclosed for using a precision ultrasound scanning device to image the anterior segment of the human eye, automatically locate the scleral spur, and, using the scleral spur as a fiduciary, to automatically make measurements in front of and behind the iris. The scleral spur can be used as a fiduciary to make measurements that characterize the normal and abnormal shapes of components within this region of the anterior segment of the eye. One or more of the measurements of the iridocorneal angle and the anterior chamber depth can be related to other measurements behind the iris including the iris lens contact distance, the iris zonule distance and the trabecular ciliary process distance. Over a period of time, these measurements can change and can indicate a change, or be a precursor for a change, of intraocular pressure (IOP), and therefore can determine an earlier onset of glaucoma.

20 Claims, 25 Drawing Sheets

(56) References Cited

U.S. PATENT DOCUMENTS

| | | | |
|---|---|---|---|
| 6,887,203 B2 | 5/2005 | Phillips et al. | |
| 7,048,690 B2 | 5/2006 | Coleman et al. | |
| 8,317,702 B2 | 11/2012 | Yu et al. | |
| 8,510,883 B2 | 8/2013 | Eilers et al. | |
| 8,758,252 B2 | 6/2014 | Eilers et al. | |
| 8,967,810 B1 * | 3/2015 | Prager | A61B 3/117 351/246 |
| 9,039,623 B2 | 5/2015 | Eilers et al. | |
| 9,597,059 B2 | 3/2017 | Watson et al. | |
| 2009/0192389 A1 * | 7/2009 | Eilers | A61B 8/4254 600/459 |
| 2016/0074007 A1 * | 3/2016 | Fedor | A61F 2/16 600/452 |
| 2016/0157817 A1 * | 6/2016 | Tanassi | A61B 8/40 600/439 |

OTHER PUBLICATIONS

Ishikawa et al. "Anterior segment imaging: ultrasound biomicroscopy," Ophthalmology Clinics of North America, Mar. 2004, vol. 17, No. 1, pp. 7-20.

* cited by examiner

Fig. 5a
Fig. 5b
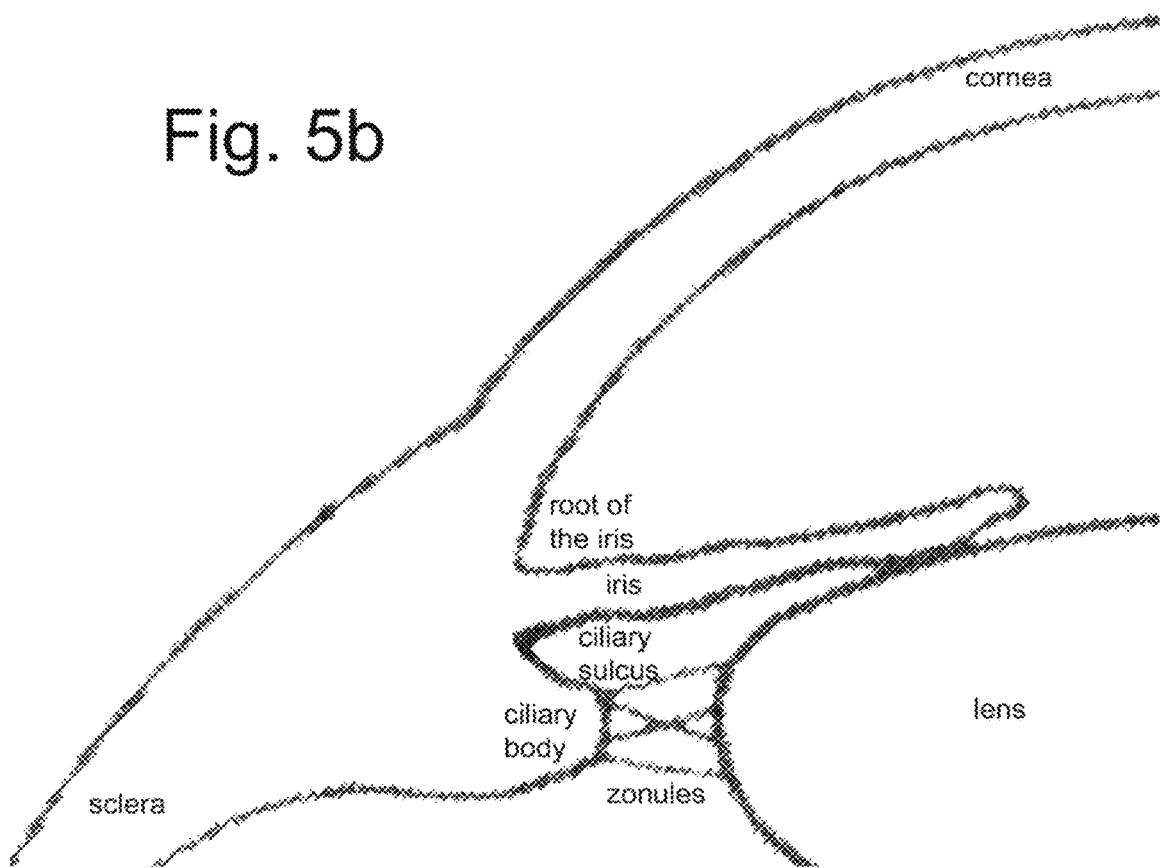

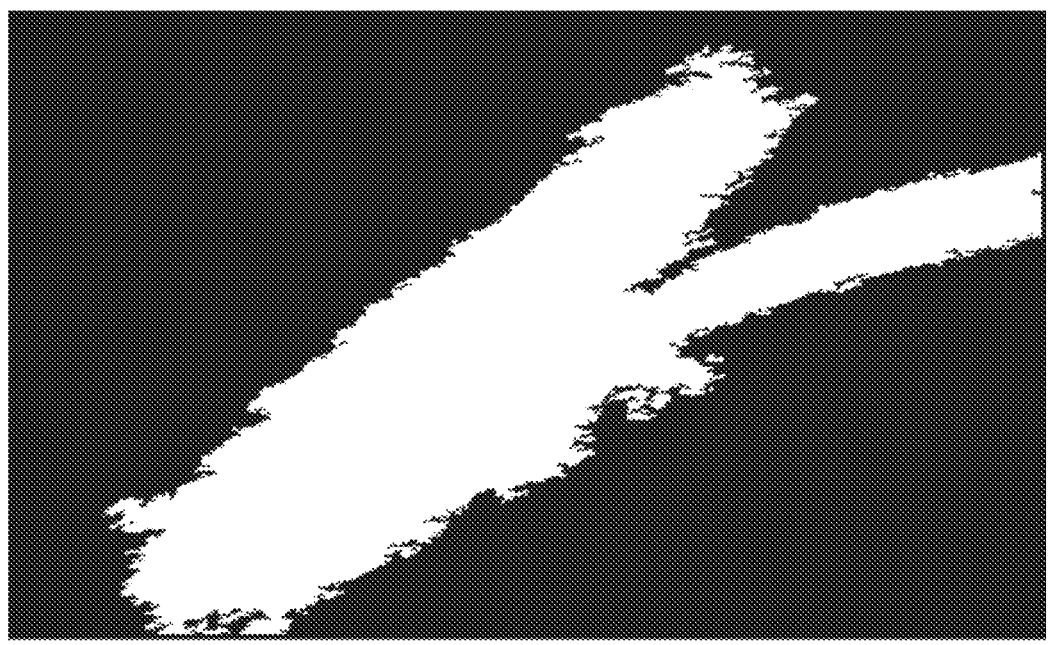
Fig. 6a
Fig. 6b
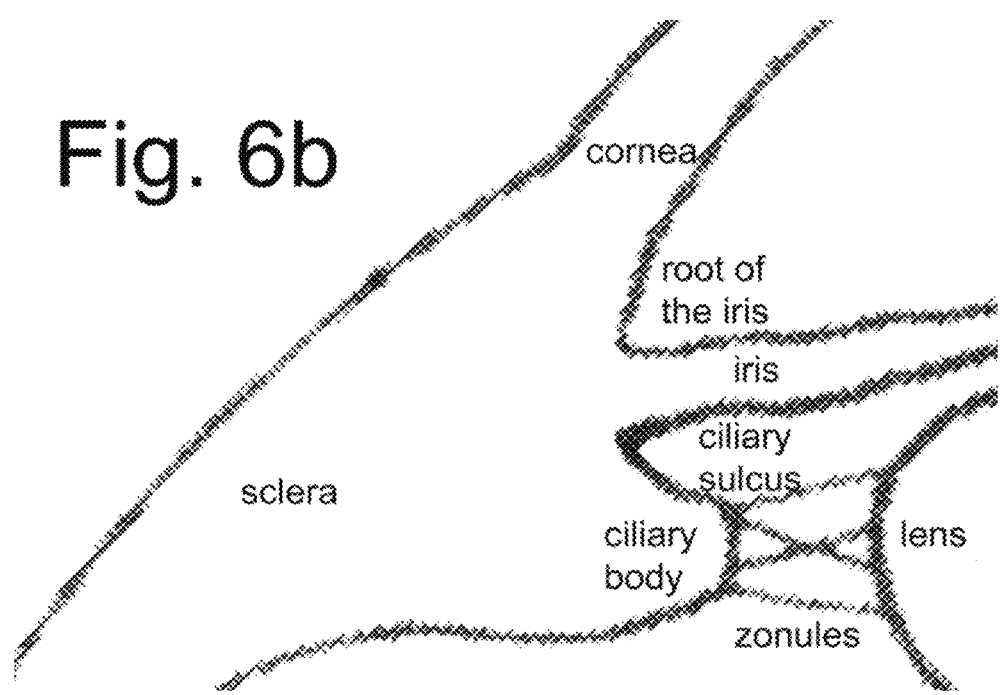

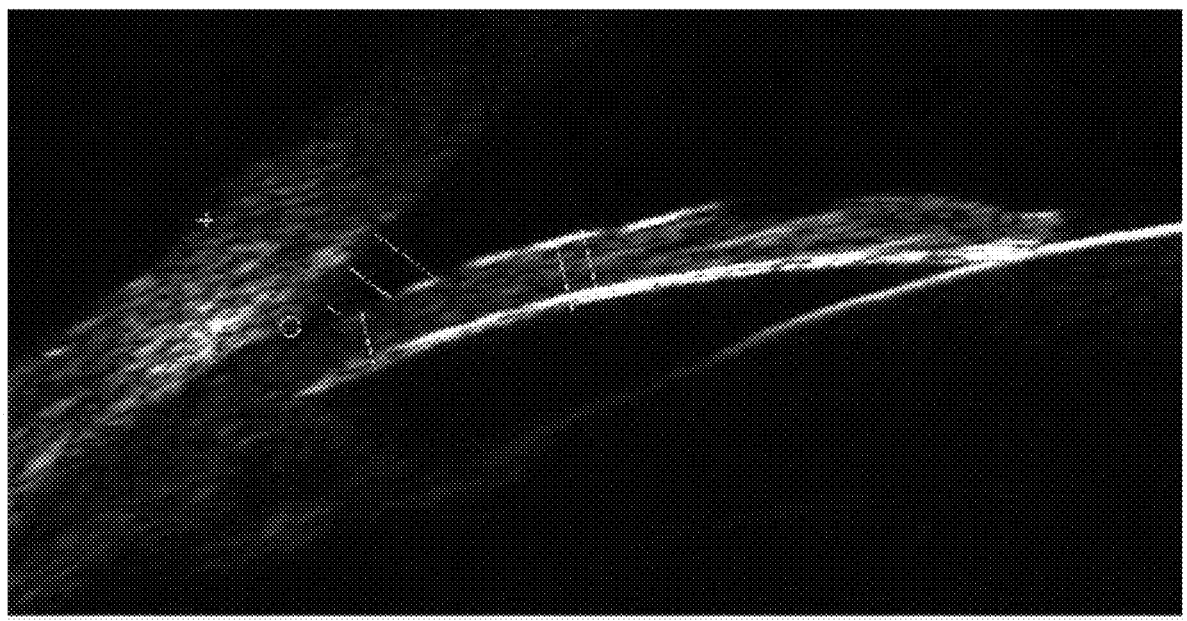
Fig. 12a
Fig. 12b
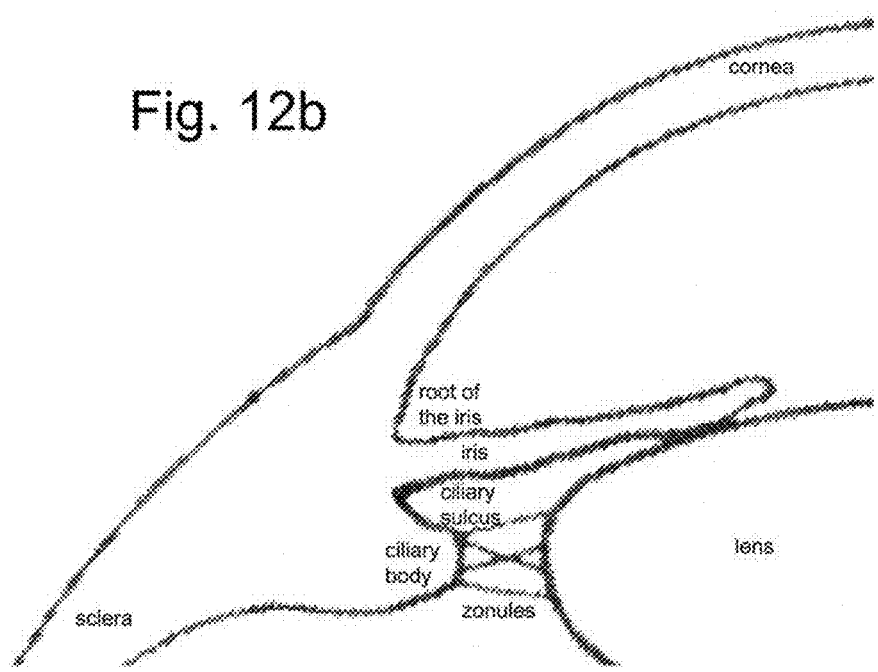

METHOD FOR MEASURING BEHIND THE IRIS AFTER LOCATING THE SCLERAL SPUR

CROSS-REFERENCE TO RELATED APPLICATIONS

This application claims the benefits, under 35 U.S.C. § 119(e), of U.S. Provisional Application Ser. No. 62/676,175 entitled "A Method for Locating the Scleral Spur in an Eye Using an Ultrasound Scanning Device" filed May 24, 2018 which is incorporated herein by reference.

FIELD OF INVENTION

The present invention relates to a method, using a precision ultrasound scanning device, for imaging the anterior segment of the eye, for automatically locating the scleral spur in a human eye and, using the scleral spur as a fiduciary, automatically making measurements in front of and behind the iris.

BACKGROUND OF THE INVENTION

To improve upon the subjectivity of gonioscopy, there has been an effort to better diagnose the onset and progression of glaucoma by imaging the anterior segment of the eye using optical and ultrasound instruments. Both of these technologies utilize the scleral spur as a distinct landmark or fiduciary from which to make measurements of one of more of the iridocorneal angle, the anterior chamber depth, the iris/lens contact distance, the iris/zonule distance and the trabecular ciliary process distance.

Optical Coherence Tomography (OCT) is a light-based imaging technology that can image most of the cornea. OCT cannot see clearly behind the scleral wall or at all behind the iris and is therefore of reduced use in screening for the early onset of glaucoma. OCT does well for imaging the central retina although only to the lateral extent allowed by a dilated pupil. These OCT images have a resolution of about 18 microns ("The Effect of Scleral Spur Identification Methods on Structural Measurements by Anterior Segment Optical Coherence Tomography", Seager, Wang, Arora, Quigley, Journal of Glaucoma, Vol. 23, No 1, January 2014, which is incorporated herein by reference.)

Ultrasound Bio Microscopy is currently the most common means of ultrasound imaging. This is applied by a hand-held device commonly known as a UBM. A UBM can capture anterior segment images using a transducer to emit very high frequency acoustic pulses ranging from about 20 to about 80 MHz. The device is normally used with an open scleral shell filled with saline which is placed on an anesthetized eye and the UBM probe is held in the saline. Alternately, a Prager cup can be used. The procedure using a UBM is somewhat uncomfortable for the patient and the pressure of the UBM on the cornea can distort the cornea and eyeball.

The UBM method is capable of making qualitative ultrasound images of the anterior segment of the eye but cannot make accurate, precision, comprehensive, measurable images of the cornea, lens or other components of the eye required for glaucoma screening, keratoconus evaluation or lens sizing. This is because of two reasons. First, the UBM is a hand-held device and relies on the steadiness of the operator's hand to maintain a fixed position relative to the eye being scanned for several seconds. Second, the UBM is pressed firmly onto the patient's eye to make contact with the patient's cornea to obtain good acoustic coupling. This gives rise to some distortion of the cornea and the eyeball.

Between these two limitations, the resolution is limited to the range of about 40 to 60 microns and the reproducibility can be no better than 20 microns ("Ultrasound Biomicroscopy in Plateau Iris Syndrome", Pavlin, Ritch and Foster, American Journal of Ophthalmology 113:390-395, April 1992 which is incorporated herein by reference).

Ultrasonic imaging using an arc scanner has found use in accurate measurement of structures of the eye, such as, for example, the cornea and lens capsule. Such measurements provide an ophthalmic surgeon valuable information that can be used to guide various surgical procedures for correcting refractive errors in LASIK and lens replacement procedures. They also provide diagnostic information after surgery to assess the geometrical location of corneal features such as the LASIK scar and lens features such as the lens connection to the ciliary muscle, lens position and lens orientation Except for on-axis measurements, dimensions and locations of eye components behind the iris cannot be readily determined by optical means. Precision ultrasound imaging with an arc scanner in the frequency range of about 5 MHz to about 80 MHz can be applied to make accurate and precise measurements of structures of the eye, such as the cornea, lens capsule, ciliary muscle and the like.

Precision ultrasound imaging using an arc scanning device (for example as described in U.S. Pat. No. 8,317,702, which is incorporated herein by reference) has a resolution of about 20 microns and a reproducibility of about 2 microns.

Ultrasonic imaging can be used to provide the required accurate images in the corner of the eye in the region around the junction of the cornea, the sclera and the iris (in the region of the suprachoroidal space to the scleral spur) which is well off-axis and essentially inaccessible to optical imaging. Other new procedures such as implantation of stents in or near the suprachoroid may provide part or all of a treatment for glaucoma The region of the eye where the cornea, iris, sclera and ciliary muscle are all in close proximity is shown in FIGS. 1 and 2 which illustrate the iridocorneal angle, scleral spur, trabecular mesh and ciliary process for example.

The arc scanning ultrasound system is capable of accurately moving an ultrasound transducer with respect to a known reference point on a patient's head. Further improvements allow for tracking of unintended eye motions during scanning as disclosed in U.S. Pat. No. 9,597,059 entitled "Tracking Unintended Eye Movements in an Ultrasonic Scan of the Eye", which is incorporated herein by reference.

Precision ultrasonic imaging requires a liquid medium to be interposed between the object being imaged and the transducer, which requires in turn that the eye, the transducer, and the path between them be at all times be immersed in a liquid medium. An eyepiece serves to complete a continuous acoustic path for ultrasonic scanning, that path extending from the transducer to the surface of the patient's eye. The eyepiece also separates the water in which the patient's eye is immersed from the water in the chamber in which the ultrasound transducer and guide track assembly are contained. Finally, the eyepiece provides a steady rest for the patient and helps the patient to remain steady during a scan. To be practical, the eyepiece should be free from frequent leakage problems, should be comfortable to the patient and its manufacturing cost should be low since it should be replaced for every new patient.

The approach of the precision ultrasound scanning device of the present disclosure is to detect the onset of glaucoma by imaging structural changes in the anterior segment before any retinal damage occurs so that the disease can be identified and successfully treated with drugs and/or stent implants.

There remains, therefore, a need for a precision ultrasound scanning device to provide a means for automatically locating the scleral spur in an eye by imaging through the scleral wall and through the iris so that accurate and repeatable measurements can be automatically made referencing from the position of the scleral spur. These measurements may improve the detection of changes in the eye that can precede elevation of intraocular pressure (IOP) that characterizes the onset of glaucoma.

SUMMARY OF THE INVENTION

These and other needs are addressed by the present disclosure. The various embodiments and configurations of the present disclosure are directed generally to ultrasonic imaging of biological materials such as the cornea, sclera, iris, lens, ciliary process etcetera in the anterior segment of an eye and in particular directed to a method for automatically locating the scleral spur in an eye using a form of segmentation analysis, and, using the scleral spur as a fiduciary, automatically making measurements in front of and behind the iris.

One of the applications of a precision ultrasound scanning device or instrument is to image the region of the eye where the cornea, iris, sclera and ciliary muscle are all in close proximity (see FIGS. 1 and 2). By using a knowledge of the structure of the eye in this region and employing unique binary filtering techniques, the position of the scleral spur can be automatically determined. Once the position of the scleral spur is determined, it can be used as a fiduciary to automatically make a number of measurements that characterize the normal and abnormal shapes of components within this region of the anterior segment of the eye. Over a period of time, these measurements can change and can indicate a change, or be a precursor for a change, of intraocular pressure (IOP).

IOP is the pressure in the eye created by the balance between continual renewal of fluids within the eye and drainage of fluids from the eye. The intraocular pressure is normally stable (fluid generated equals fluid drained) but can increase when Schlemm's canal and trabecular mesh through which the fluid normally drains becomes progressively blocked. Increasing IOP is a sign of the onset of glaucoma and, if left untreated, elevated IOP causes damage to the retinal cones leading to progressive loss of sight. This process beginning with blocked drainage and ending in damage to the retina and blindness is known as glaucoma.

IOP can be measured with a goniometer (another purpose of gonioscopy is to visualize the iridocorneal angle (or simply "angle"). However, changes in the measurements that can be made as disclosed herein can be precursors to a measurable change in IOP and therefore can allow the ophthalmologist to take preventative measures to prevent the progression of glaucoma. The method disclosed herein comprises the following principal steps which are performed automatically:
1. Acquire B-Scans
2. Binarize B-Scans
3. Determine the iris/lens contact distance (ILCD) and anterior chamber depth (ACD)
4. Locate Root of the Iris
5. Locate Root of the Ciliary Sulcus
6. Isolate the Sclera
6. Locate the Scleral Spur
7. Using the scleral spur as a fiduciary, make measurements including, at least, the trabecular/iris angle (TIA), the iris lens contact distance, the iris zonule distance (IZD) and the trabecular ciliary process distance (TCPD).
8. Prepare an Automated based on a B-Scan with all measurements displayed.

One or more of the measurements of the angle and the anterior chamber depth may be related to one or more of the measurements behind the iris of the iris lens contact distance, the iris zonule distance and the trabecular ciliary process distance. If so, these measurements can then serve as an early indicators of increasing IOP and therefore can determine an earlier onset of glaucoma as compared to the conventional measurement of IOP using a goniometer.

A method is disclosed for detecting a scleral spur in an eye of a patient. The method comprises providing an ultrasound device having a scan head with an arcuate guide track and a carriage movable along the arcuate guide track; an eyepiece configured to maintain the eye of the patient in a fixed location with respect to the arcuate guide track; and a transducer connected to the carriage. The method includes emitting, from the transducer, ultrasound pulses as the carriage moves along the arcuate guide track; storing the received ultrasound pulses on a non-transitory computer readable medium; forming, by at least one electronic device, a B-Scan of the eye of the patient based on the received ultrasound pulses; binarizing, by the at least one electronic device, the B-Scan from a grayscale color palette to a black/white color palette; determining, by the at least one electronic device, an average surface of a sclera of the eye; and locating, by the at least one electronic device, a bump of the average surface of the sclera that corresponds to the scleral spur.

A system is disclosed for detecting a scleral spur in an eye of a patient, comprising an ultrasound device, having a scan head having an arcuate guide track and a carriage movable along the arcuate guide track; an eyepiece configured to maintain the eye of the patient in a fixed location with respect to the arcuate guide track; a transducer connected to the carriage, wherein ultrasound pulses are emitted into the eye of the patient and the received ultrasound pulses are stored on a non-transitory computer readable medium; wherein at least one electronic device has non-transitory readable medium and has instructions that, when executed, cause the at least one electronic device to form a B-Scan of the eye of the patient based on the received ultrasound pulses; binarize the B-Scan from a grayscale color palette to a black/white color palette; determine an average surface of a sclera of the eye; and locate a bump of the average surface of the sclera that corresponds to the scleral spur.

Another system is disclosed for binarizing a B-Scan of an eye of a patient, comprising an ultrasound device, having a scan head having an arcuate guide track and a carriage movable along the arcuate guide track; an eyepiece configured to maintain the eye of the patient in a fixed location with respect to the arcuate guide track; a transducer connected to the carriage, wherein ultrasound pulses are emitted into the eye of the patient, and wherein the received ultrasound pulses are stored on a non-transitory computer readable medium and wherein at least one electronic device having the non-transitory readable medium and having instructions that, when executed, cause the at least one electronic device to form a B-Scan of the eye of the patient based on the received ultrasound pulses; to determine an average intensity of a grayscale color palette of the B-Scan of the eye; to binarize the B-Scan of the eye from the grayscale color palette to a black/white color palette, wherein discrete areas of the B-Scan above a predetermined intensity are binarized to white and discrete areas of the B-Scan below the predetermined intensity are binarized to black, and the predetermined intensity depends on the average intensity.

The following definitions are used herein:

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

Accuracy as used herein means substantially free from measurement error.

The angle as referred to herein is the angle between the iris, which makes up the colored part of the eye, and the cornea, which is the clear-window front part of the eye. The angle is short for the iridocorneal angle. When the angle is open, most, if not all, of the eye's drainage system can be seen by using a special mirrored lens. When the angle is narrow, only portions of the drainage angle are visible, and in acute angle-closure glaucoma, none of it is visible. The angle is the location where the fluid that is produced inside the eye, the aqueous humor, drains out of the eye into the body's circulatory system. The function of the aqueous humor is to provide nutrition to the eye and to maintain the eye in a pressurized state. Aqueous humor should not be confused with tears, since aqueous humor is inside the eye.

The angle of opening, called the trabecular-iris angle (TIA), is defined as an angle measured with the apex in the iris recess and the arms of the angle passing through a point on the trabecular meshwork 500 µm from the scleral spur and the point on the iris perpendicularly. The TIA is a specific way to measure the angle or iridocorneal angle.

The anterior segment comprises the region of the eye from the cornea to the back of the lens.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

In this disclosure, binarize means to convert grayscale pixels to black or white depending on which side of a selected grayscale threshold the pixel is on, where grayscale pixels range in values from 0 (black) to 255 (white).

Binary filtering or binary thresholding is used to transform an image into a binary image by changing the pixel values according to a selection rule. The user defines two thresholds and two intensity values. For each pixel in the input image, the value of the pixel is compared with the two thresholds. If the pixel value is inside the range defined by the two thresholds, the output pixel is assigned as an inside value. Otherwise the output pixels are assigned to an outside value.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

The bump as referred to herein is the protruding structure located at the intersection of the interface curve and the curve formed by the posterior of the cornea.

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Fiducial means a reference, marker or datum, such as a point or line, in the field of view of an imaging device used as a fixed standard of reference for a fixed basis of comparison or measurement.

Glaucoma is a group of eye conditions that damage the optic nerve, the health of which is vital for good vision. This damage is often caused by an abnormally high pressure in the eye. Glaucoma is one of the leading causes of blindness for older people. Glaucoma is often linked to a buildup of pressure inside the eye.

In this disclosure, grayscale means an image in which the value of each pixel is a single sample representing only intensity information. Images of this sort are composed exclusively of shades of gray, varying from black at the weakest intensity to white at the strongest intensity. Grayscale images are commonly stored with 8 bits per sampled pixel. This pixel depth allows 256 different intensities (shades of gray) to be recorded where grayscale pixels range in values from 0 (black) to 255 (white).

The home position of the imaging ultrasound transducer is its position during the registration process.

Intraocular pressure (IOP) is the pressure in the eye created by the continual renewal and drainage of fluids within the eye. The intraocular pressure is normally stable but can increase because the canal and trabecular mesh through which the fluid normally drains becomes progressively blocked. Increasing IOP is a sign of the onset of glaucoma and, if left untreated, causes damage to the retinal cones leading to progressive loss of sight which is known as glaucoma.

The iridocorneal angle is referred to herein as the angle between the iris, which makes up the colored part of the eye, and the cornea, which is the clear-window front part of the eye. The iridocorneal angle is often referred to as the angle.

The iris dilator muscle is a smooth muscle of the eye, running radially in the iris which serves as a dilator. When the sphincter pupillae contract, the iris decreases or constricts the size of the pupil. The iris is a pigmented disk with a variable aperture which controls the size of the pupil and the amount of light reaching the retina. The iris comprises the anterior limiting layer, the stroma, the dilator muscle layer, and the posterior pigmented epithelium.

In this disclosure, isolating as applied to a binarized image means to isolate the scleral material containing the scleral spur from iris, cornea and ciliary material.

In this disclosure, a moving average (also referred to as a rolling average or running average) is a way of analyzing data points by creating a series of averages of different subsets of adjacent data points in the full data set.

The natural lens (also known as the crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Optical as used herein refers to processes that use light rays.

The optical axis of the eye is a straight line through the centers of curvature of the refracting surfaces of an eye (the anterior and posterior surfaces of the cornea and lens).

Positioner means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Posterior means situated at the back part of a structure; posterior is the opposite of anterior.

The posterior segment comprises the region of the eye from the back of the lens to the rear of the eye comprising the retina and optical nerve.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

The pulse transit time across a region of the eye is the time it takes a sound pulse to traverse the region.

Refractive means anything pertaining to the focusing of light rays by the various components of the eye, principally the cornea and lens.

Registration as used herein means aligning.

ROI means Region of Interest.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

The scleral spur in the human eye is an annular structure composed of collagen in the anterior chamber. The scleral spur is a fibrous ring that, on meridional section, appears as a wedge projecting from the inner aspect of the anterior sclera. The spur is attached anteriorly to the trabecular meshwork and posteriorly to the sclera and the longitudinal portion of the ciliary muscle.

Sector scanner is an ultrasonic scanner that sweeps a sector like a radar. The swept area is pie-shaped with its central point typically located near the face of the ultrasound transducer.

Segmentation analysis as used in this disclosure means manipulation of an ultrasound image to determine the boundary or location of an anatomical feature of the eye.

In this disclosure, smoothing as applied to a selected surface of a binarized image means to prepare the surface to be characterized by a straight line by removing protrusions above a first selected threshold and recesses below a second selected threshold. This is a special case of segmentation analysis.

The ciliary sulcus is the groove between the iris and ciliary body. The scleral sulcus is a slight groove at the junction of the sclera and cornea.

In the human eye, the scleral spur is an annular structure composed of collagen. It is a protrusion of the sclera into the anterior chamber. The scleral spur is the most anterior projection of the sclera internally. It is a circular ridge of sclera on the internal aspect of the corneoscleral junction. On cross-section, it appears as a hooklike process deep to the scleral venous sinus; relatively rigid, it provides attachment for the meridional fibers of the ciliary body.

Schlemm's canal is a circular lymphatic-like vessel in the eye that collects aqueous humor from the anterior chamber and delivers it into the episcleral blood vessels via aqueous veins. Schlemm's canal is a unique vascular structure that functions to maintain fluid homeostasis by draining aqueous humor from the eye into the systemic.

The Schwalbe line is the line formed by the posterior surface of the cornea, and delineates the outer limit of the corneal endothelium layer.

Sessile means normally immobile.

The suprachoroid lies between the choroid and the sclera and is composed of closely packed layers of long pigmented processes derived from each tissue.

The suprachoroidal space is a potential space providing a pathway for uveoscleral outflow and becomes an actual space in choroidal detachment. The hydrostatic pressure in the suprachoroidal space is an important parameter for understanding intraocular fluid dynamics and the mechanism of choroidal detachment.

The trabecular meshwork is an area of tissue in the eye located around the base of the cornea, near the ciliary body, and is responsible for draining the aqueous humor from the eye via the anterior chamber (the chamber on the front of the eye covered by the cornea). The trabecular meshwork, plays a very important role in the drainage of aqueous humor. The majority of fluid draining out of the eye is via the trabecular meshwork, then through a structure called Schlemm's canal, into collector channels, then to veins, and eventually back into body's circulatory system.

In this disclosure, thresholding means to select a threshold and divide objects into those above the threshold and those below the threshold.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

An ultrasonic arc scanner is an ultrasound scanning device utilizing a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

The visual axis of the eye is a straight line that passes through both the center of the pupil and the center of the fovea.

Zonules are tension-able ligaments extending from near the outer diameter of the crystalline lens. The zonules attach the lens to the ciliary body which allows the lens to accommodate in response to the action of the ciliary muscle.

BRIEF DESCRIPTION OF THE DRAWINGS

The present invention may take form in various components and arrangements of components, and in various steps and arrangements of steps. The drawings are only for purposes of illustrating the preferred embodiments and are not to be construed as limiting the invention. In the drawings, like reference numerals may refer to like or analogous components throughout the several views.

FIG. 5A is a binarized image of the B-scan of a part of the anterior segment.

FIG. 5B is a diagram of the anatomy of the eye.

FIG. 6A is a binarized image of the region of interest containing the scleral spur.

FIG. 6B is a diagram of the anatomy of the eye.

FIG. 12A is a B-scan of half of the anterior segment showing the location of features to be measured.

FIG. 12B is a diagram of the anatomy of the eye.

DETAILED DESCRIPTION OF THE DRAWINGS

One of the applications of a precision ultrasound scanning device or instrument is to image the region of the eye around the confluence of the cornea, iris, sclera and ciliary muscle. By using a knowledge of the structure of the eye in this region along with binary filtering techniques, the position of the scleral spur can be determined with respect to a known point (the visual axis intersection with the anterior or posterior cornea, for example). Once the position of the scleral spur is determined, a number of measurements that characterize the normal and abnormal shapes of components within the anterior segment of the eye can be made. Over a period of time, these measurements can change and can indicate a change or be a precursor to a change of intra ocular pressure (IOP).

IOP is the pressure in the eye created by the continual renewal of fluids within the eye and drainage of fluids from the eye. The intraocular pressure is normally stable (fluid generated equals fluid drained) but can increase when the canal and trabecular mesh through which the fluid normally drains becomes progressively blocked. Increasing IOP is a sign of the onset of glaucoma and, if left untreated, causes damage to the retinal cones leading to progressive loss of sight which is known as glaucoma.

IOP can be measured with a goniometer. However, changes in the measurements that can be made as disclosed herein can be precursors to a measurable change in IOP and therefore can allow the ophthalmologist to take preventative measures to prevent the progression of glaucoma before permanent damage to the retina occurs.

The following measurements as denoted by their abbreviations are referenced in this disclosure:

ACD which is the anterior chamber depth

AOD which is the angle opening distance 500 (500 microns from the scleral spur)

ID which is the iris thickness (must measure through the iris)

ILCD which is the iris lens contact distance (must measure through the iris)

IZD which is the iris zonule distance (must measure through the iris)

ROI which is the Region of Interest.

TCPD which is the trabecular ciliary process distance (must measure through the iris)

TIA is the trabecular iris space area

Figure 25A:
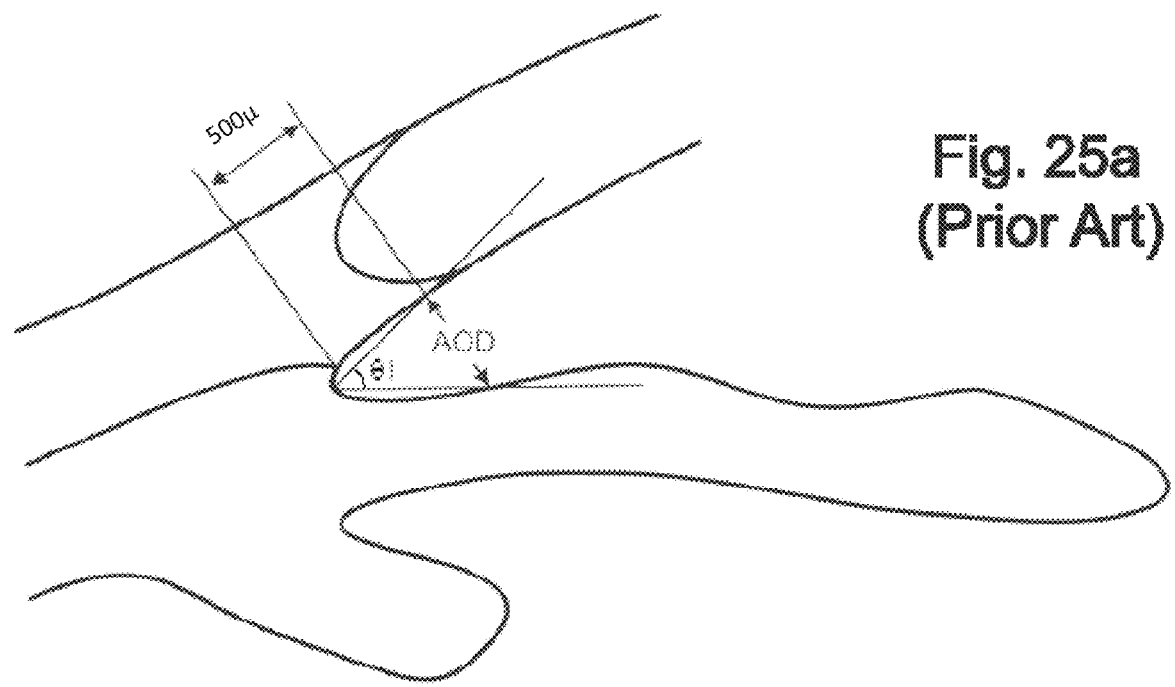
FIG. 25A illustrates various measurements that can be made using ultrasound technology.
Figure 25B:
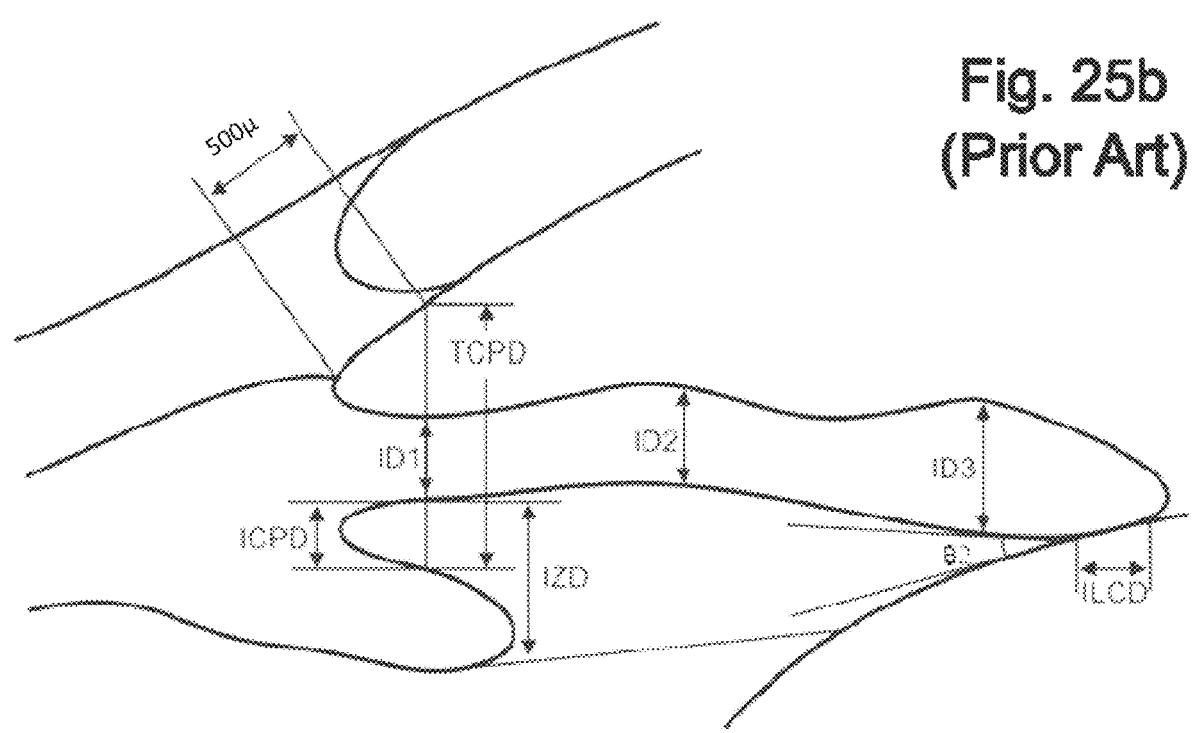
FIG. 25B illustrates various measurements that can be made using ultrasound technology.

These measurements are illustrated in FIGS. 25A and 25B and are discussed in "Anterior Segment Imaging: Ultrasound Biomicroscopy", Hiroshi Ishikawa, MD* and Joel S. Schuman, MD, Ophthalmol Clin North Am. 7-20, March 2004 which is incorporated herein by reference.

In all the figures, left and right are referenced to the page. Left and right directions are illustrated in FIG. 1.

Figure 1:
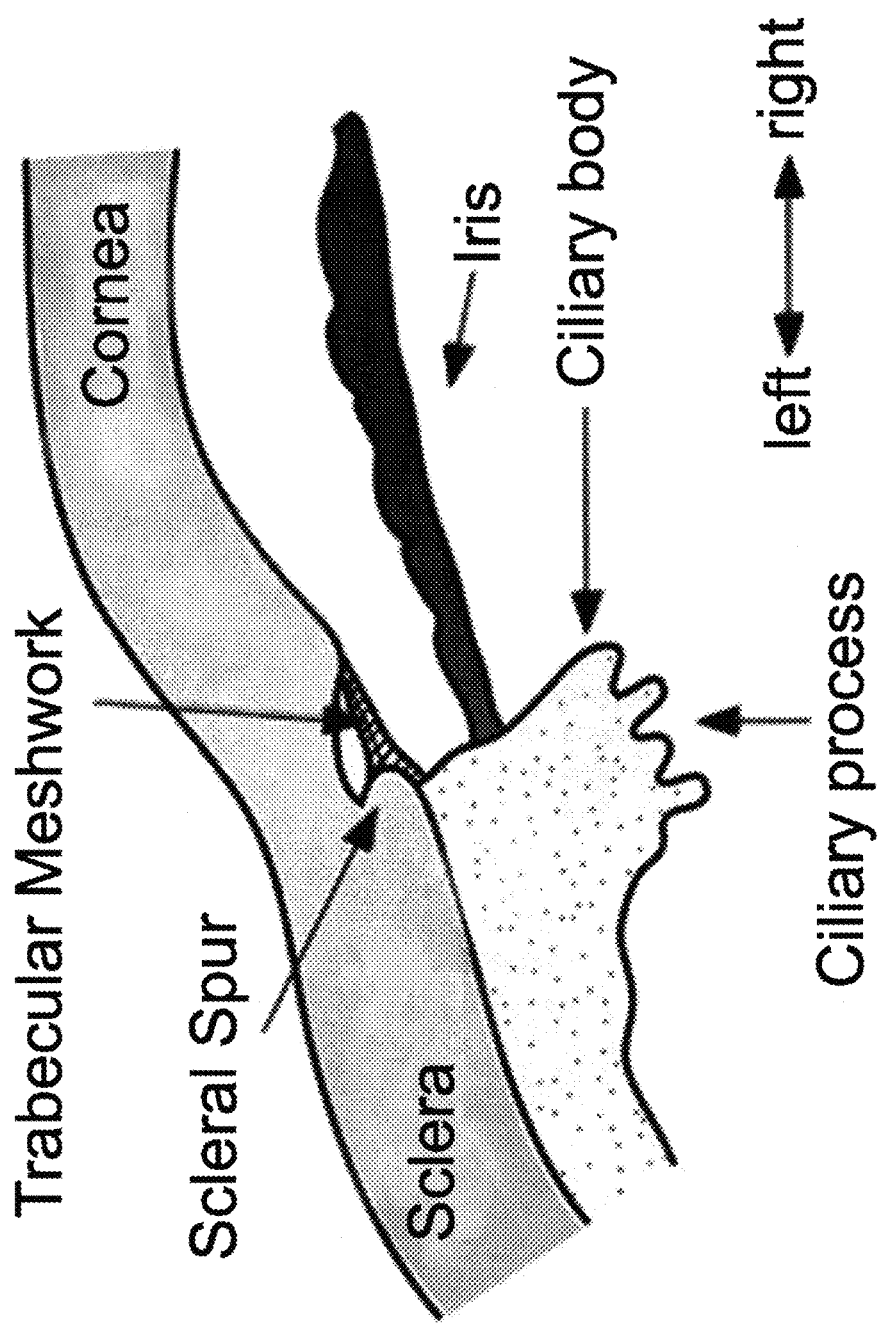
FIG. 1 shows the anatomy of the eye in the region near the scleral spur.

FIG. 1 shows the anatomy of the eye in the region near the scleral spur. This figure illustrates the geometry of the region of interest in which the scleral spur can be found. The iris, ciliary process, cornea and sclera all come together in this region. As in all subsequent figures, left and right, as shown in this figure, are referenced to the page.

Figure 2:
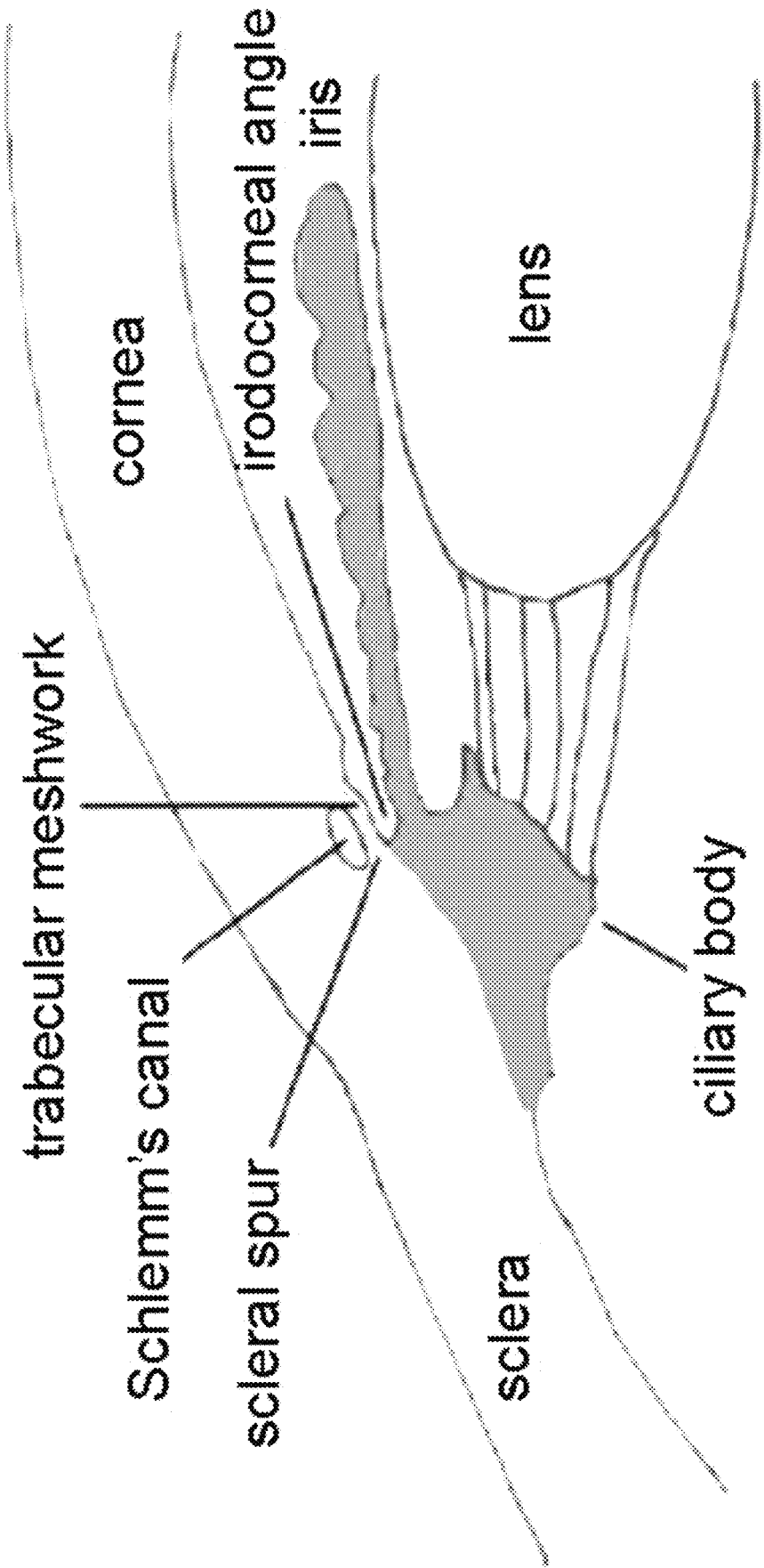
FIG. 2 shows an alternate diagram of the anatomy of the eye in the region near the scleral spur.

FIG. 2 shows an alternate diagram of the anatomy of the eye in the region near the scleral spur. The iridocorneal angle is the angle between the iris and the cornea. The iridocorneal angle is also known as simply the angle.

The following steps are performed to determine noted points of interest (including the scleral spur as a fiduciary) and the measurements dependent on those points, including points/measurements both in front of and behind the iris:

Acquire and Binarize B-Scans

Figure 3A:
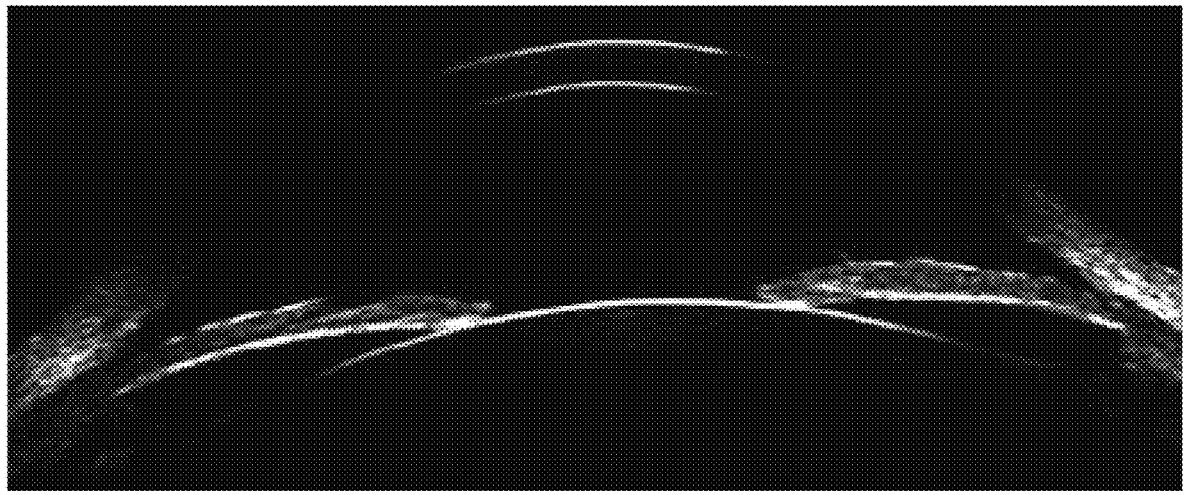
FIG. 3A is a B-scan of the anterior segment of a human eye.
Figure 3B:
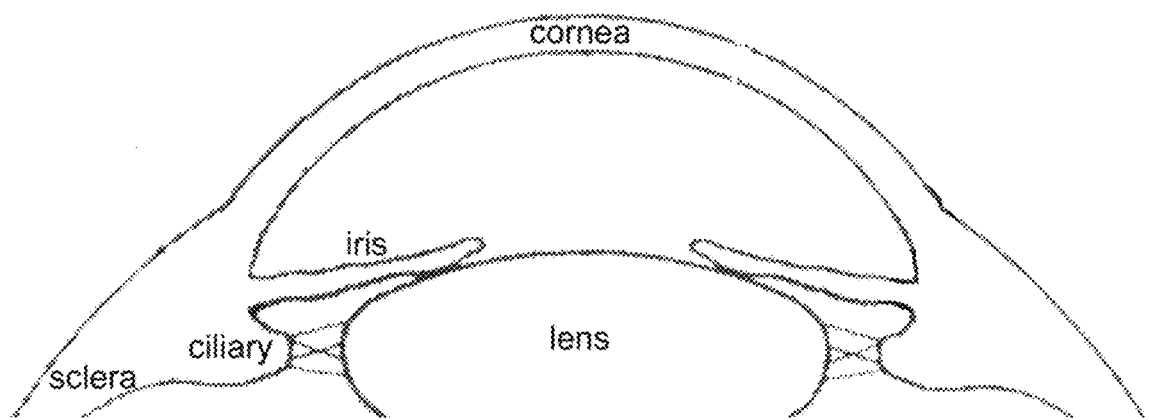
FIG. 3B is a diagram of the anatomy of the eye.

1. Using an ultrasound arc scanning device, form a B-scan image of the anterior segment (anterior cornea to approximately mid lens, wide angle sclera to sclera) including the left and right sides of the scleral/iris region. FIG. 3A is a B-scan of the anterior segment of a human eye and a line drawing of the region of the eye shown in the B-scan. This image was obtained by a precision ultrasound arc scanning device.

2. Select a threshold value from 1 to 255 for pixel intensity and form a corresponding binary image wherein pixels that are greater than or equal to the specified threshold are converted to 1 (white) and pixels that are less than the specified threshold are converted to 0 (black). Starting threshold depends on the average background pixel intensity. Threshold is then increased iteratively to identify objects of interest.

3. Eliminate extraneous objects such as the anterior lens surface, cornea, electronic noise, reflections, cataracts, etcetera. As the image is further thresholded, the region of the cornea nearest the sclera disappears, leaving the sclera and iris isolated. The same process removes the ciliary muscle at the bottom of the sclera. Part of the thresholding process comprises deleting the pixels less than the threshold value, then filling in any holes in the objects, then deleting any remaining small objects whose area, defined by the number of pixels they contain, are less than a specified area.

Figure 4:
FIG. 4 is a binarized image of the B-scan of the anterior segment.

4. Binarize the whole anterior segment image—from 0 to 255 grades of grayscale to black and white. FIG. 4 is a binarized image of a B-scan of the anterior segment and is similar to the B-scan image shown in FIG. 3A.

Determine ILCD and ACD

5. Create left and right halves of the binarized image.

FIG. 5A is a binarized image of the B-scan of the region of interest in the anterior segment for detecting the scleral spur. FIG. 5a is the B-scan image and FIG. 5b is a line drawing of the region of the eye shown in the B-scan.

FIG. 6A is a binarized image of the region of interest of the local region containing the scleral spur. FIG. 6a is the B-scan image and FIG. 6b is a line drawing of the region of the eye shown in the B-scan.

6. From the binarized B-scan, create a left and right binarized region of interest around the intersection of the lens/iris (see FIGS. 5 and 6).

Figure 7A:
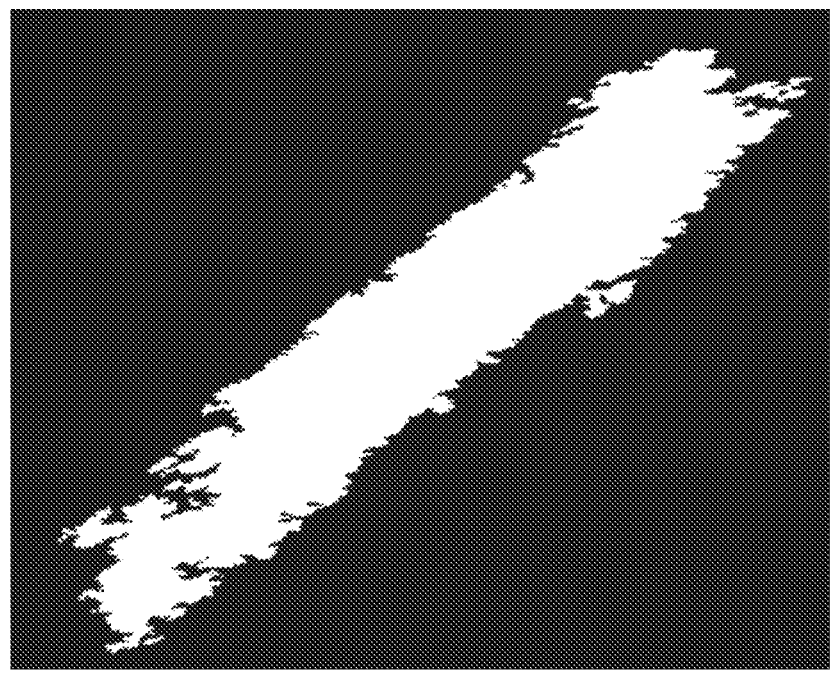
FIG. 7A is a further isolated and smoothed binarized image of the region of interest containing the scleral spur.
Figure 7B:
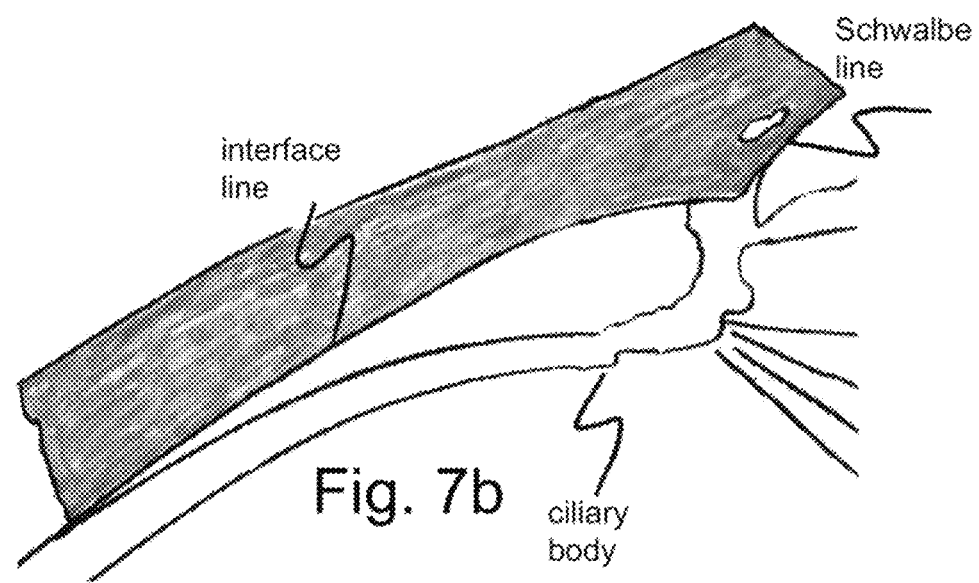
FIG. 7B is a diagram of the anatomy of the eye.

FIG. 7A is a further isolated and smoothed binarized image of the region of interest containing the scleral spur. FIG. 7a is the B-scan image and FIG. 7b is a line drawing of the region of the eye shown in the B-scan. The line drawing illustrates the interface curve formed by the interface between the sclera and ciliary muscle and the Schwalbe line which is the line formed by the posterior surface of the cornea.

Figure 8:
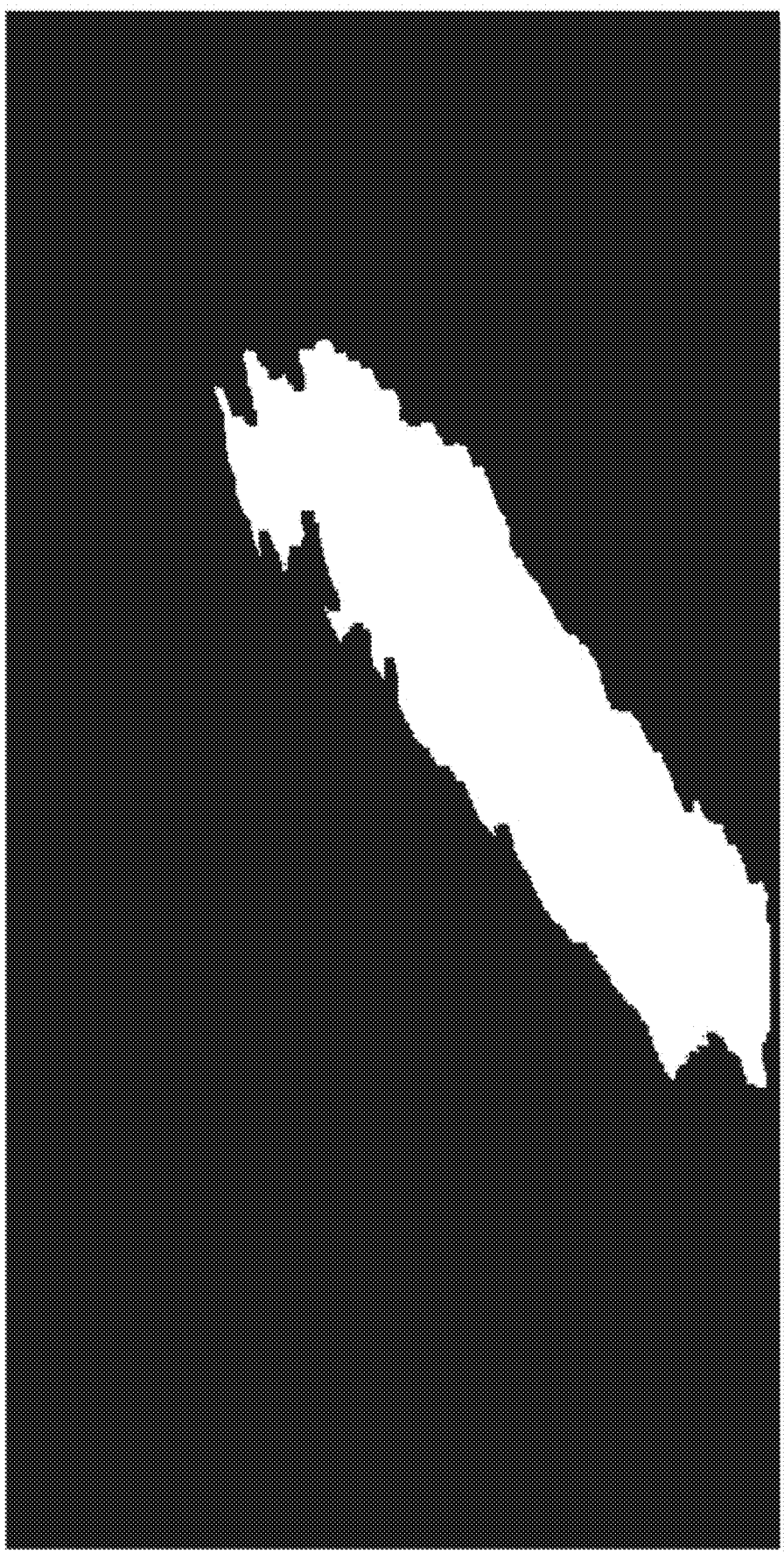
FIG. 8 is a binarized image of a close-up of a further smoothed and shortened image of the isolated sclera, including the scleral spur.

FIG. 8 is a binarized image of a close-up of a further smoothed and shortened image of the isolated sclera, including the scleral spur. This image is a further processed version of the image shown in FIG. 7A.

Figure 10A:
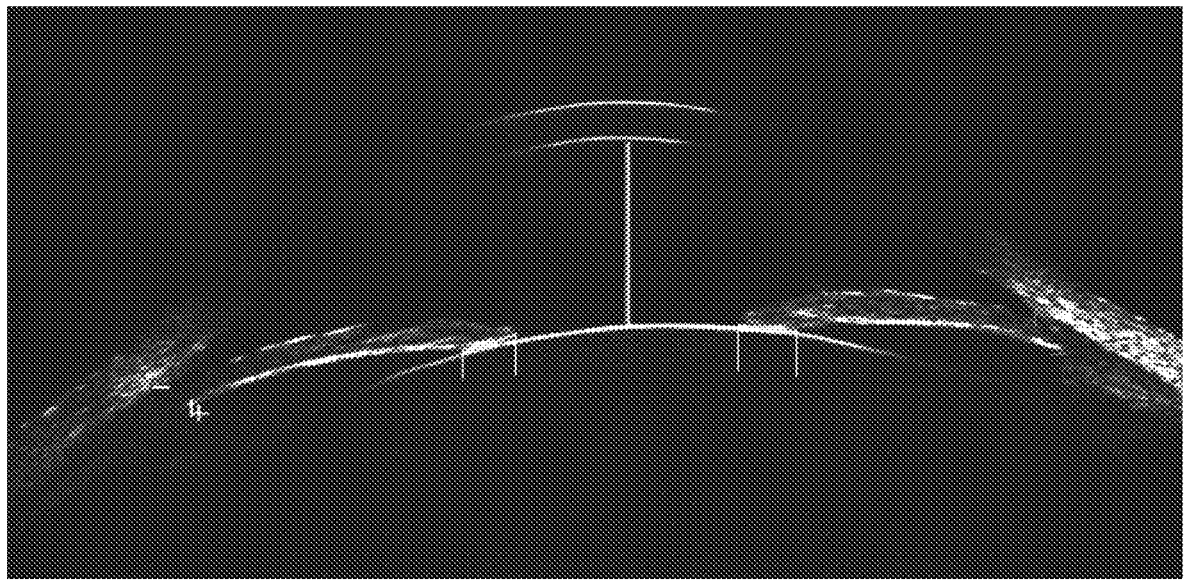
FIG. 10A is a B-scan of the anterior segment showing ACD and ILCD measurements.
Figure 10B:
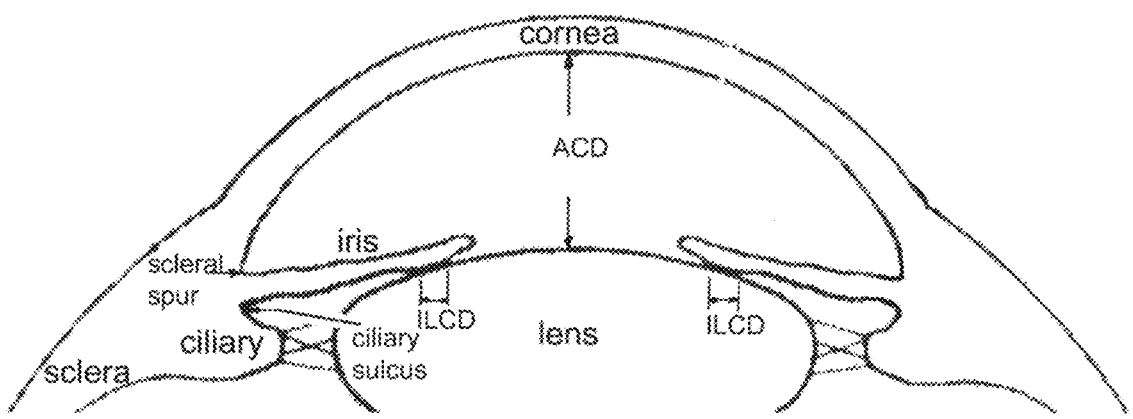
FIG. 10B is a diagram of the anatomy of the eye.
Figure 11:
FIG. 11 shows the ILCD (the iris lens contact distance) region of interest of the B-Scan for one side of the eye.

7. From each iris/lens ROI, determine the iris/lens contact distance (ILCD) on right and left sides.
  a. Using the binarized ROI, locate the center of the lens, then move outward along the top surface of the lens until detecting the iris.
  b. Keep moving outward along the lens until a gap is detected between the bottom of the iris and the lens, then determine the actual intersection of the bottom of the iris and the lens (the contact point between the iris and the lens furthest from the center of the anterior segment.)
  c. Repeat for the right side
  d. The iris-lens contact distance ("ILCD") is the distance between the first iris lens contact point and the second iris lens contact point. FIG. 11 is a B-scan of half of the anterior segment showing the location of the right and left ILCD.
  e. Determine the minimum distance from the anterior lens surface to the posterior cornea surface ("ACD"). This is illustrated in FIG. 10A which is a B-scan of the anterior segment illustrating the ACD and ILCD measurements.

Locate the Root of the Iris

Figure 9:
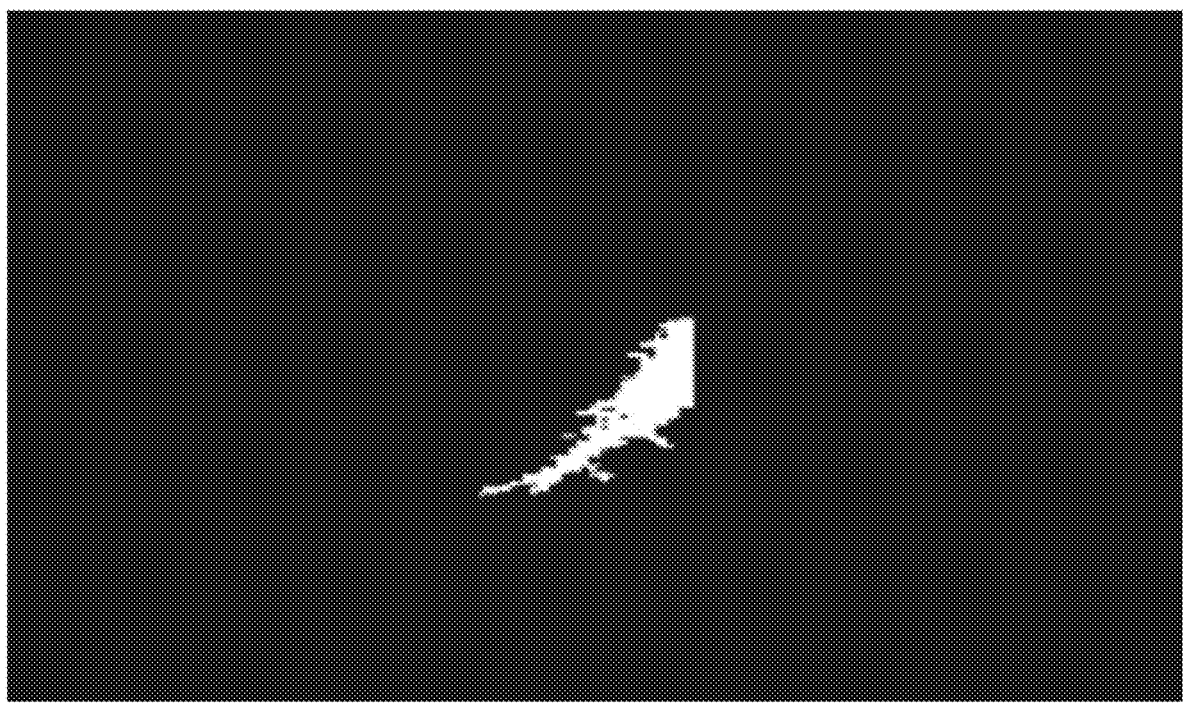
FIG. 9 is an inverted binarized image of the root of the iris.

8. Now look for the left iris root (a first region of interest)
  a. On the left, create a region of interest near where the sclera and iris meet. This binarized ROI is illustrated in FIG. 6A.
  b. Start at the right side of the region of interest and move to the left until black pixels are encountered c. Invert the polarity of the image (black vs. white). This image is illustrated in FIG. 9 which shows the inverted binarized image of the root of the iris.

d. Find the leftmost white point shown in FIG. 9 which is the root of the iris.

e. Repeat step 8 for iris root on the right side.

Locate the Root of the Ciliary Sulcus

9. Now look for the left and right ciliary sulcus roots (a second region of interest). This is the same procedure as finding the left and right roots of the iris a. On the left, create a region of interest near the iris root b. Start at the right side of the region of interest and move to the left until black pixels are encountered c. Invert the polarity of the image (black vs. white)

d. Find the leftmost white point which is the root of the ciliary sulcus e. Repeat step 9 for ciliary sulcus root on the right side

Isolate the Sclera

A limbus-parallel ring of fibers forms the inner surface of the sclera at the junction of the scleral and corneal curvatures and projects inward to inter digitate with the tendon fibers of the meridional ciliary muscle. The sessile group of limbus-parallel fibers of the sclera is called the scleral roll and the inward-projecting group of limbus-parallel fibers is the scleral spur. The scleral roll thus forms the posterior wall of the canal of Schlemm and the roll and spur together form the posterior wall of the internal scleral sulcus. The spur extends inward from the inner sclera toward the axis of the eye for about 0.09 mm. The scleral roll lies at the junction of the scleral curvature with the corneal curvature and the scleral spur lies between the meridional portion of the ciliary muscle and the trabecular mesh.

10. From the left and right side binarized images, create a binarized region of interest near the iris root. This binarized ROI is illustrated in FIG. 6A.

11. For left and right sides, further isolate the sclera from the cornea, ciliary process and iris by increasing the threshold until the sclera is separated from the other objects 12. For left and right, completely isolate sclera by deleting all objects except the sclera 13. Smooth the boundary of the isolated sclera. The isolating and smoothing steps are illustrated in FIGS. 7A and 8.

Locate the Scleral Spur

The curve formed by the interface between the lighter sclera and darker ciliary muscle is referred to herein as the "interface curve". A line projected from a point on the interface curve at the local slope is referred to herein as a "scleral slope line". The protruding structure located at the intersection of the interface curve and the curve formed by the posterior of the cornea is referred to herein as "the bump". These features are illustrated in FIGS. 22, 23, and 24A.

Figure 22:
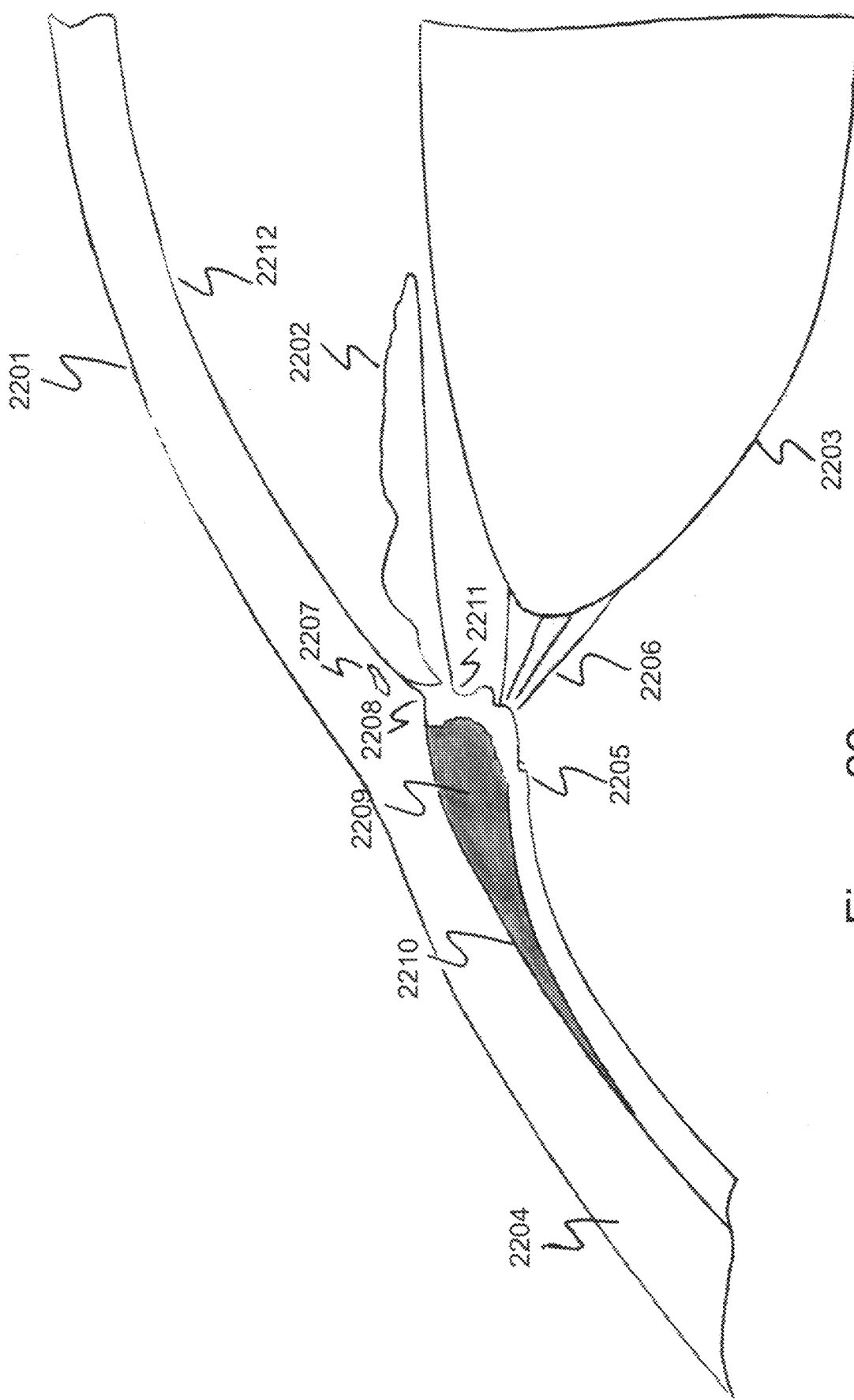
FIG. 22 illustrates geometric structures used in detecting the scleral spur.

FIG. 22 illustrates geometric structures used in detecting the scleral spur. The cornea 2201, the iris 2202, the lens 2203, the sclera 2204 and the ciliary body 2205 are the main components shown. The ciliary body 2205 includes the ciliary muscle 2209. The ciliary sulcus 2211 is shown between the iris 2202 and the ciliary body 2205. Schlemm's canal 2207 is also shown for reference. The interface curve 2210 is formed by the interface between the sclera 2204 and the ciliary muscle 2209. Interface curve 2210 intersects Schwalbe line 2212 and this intersection is called the bump 2208.

Figure 23:
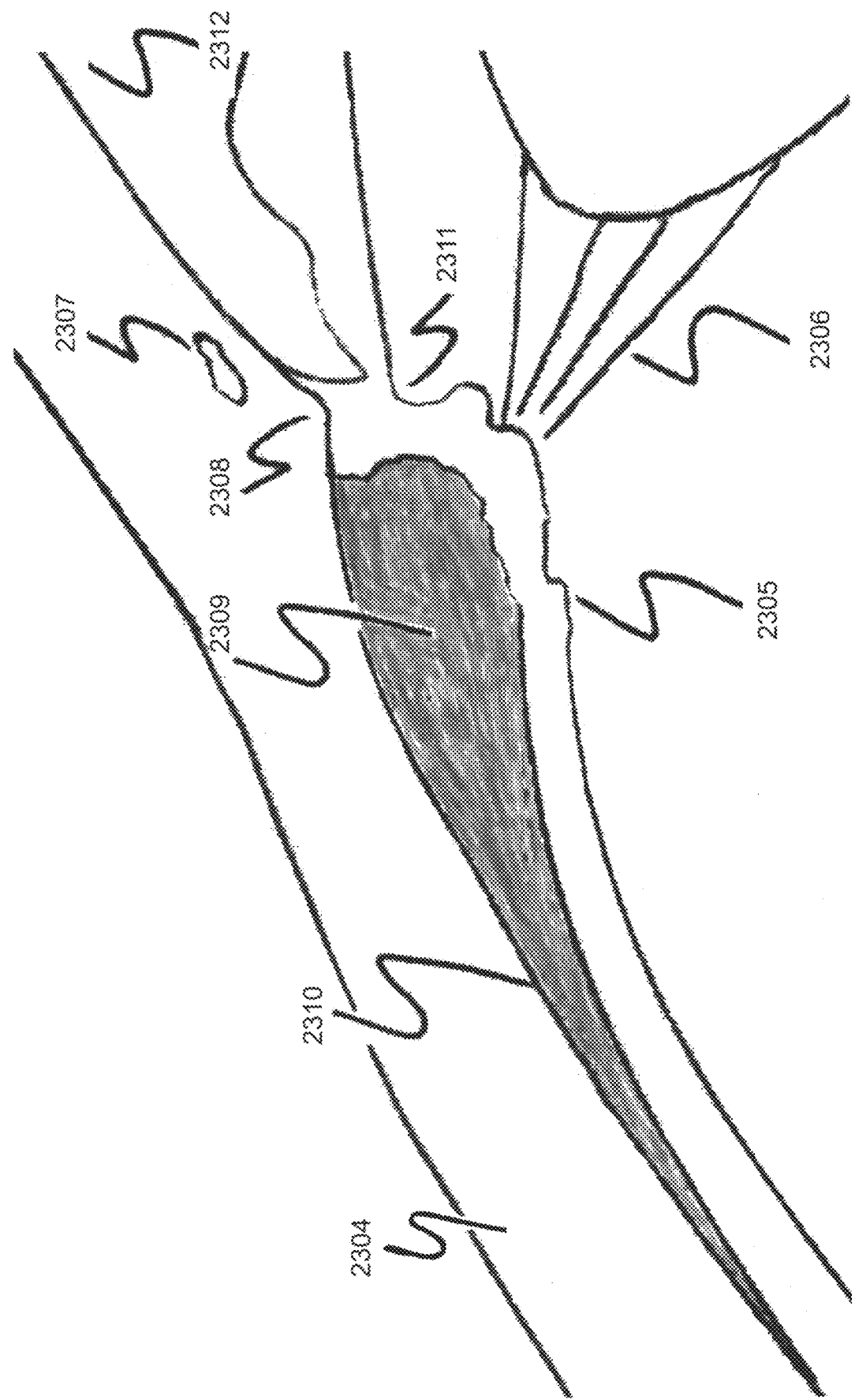
FIG. 23 is a close-up of geometric structures used in detecting the scleral spur.

FIG. 23 is a close-up of geometric structures used in detecting the scleral spur. This figure includes the sclera 2304 and the ciliary body 2305, the ciliary muscle 2309 (shaded). The ciliary sulcus 2311 is shown below the iris. Schlemm's canal 2311 is also shown for reference. The interface curve 2310 is formed by the interface between the sclera 2304 and the ciliary muscle 2309. Interface curve 2310 intersects Schwalbe line 2312 and this intersection is called the bump 2308.

Figure 24A:
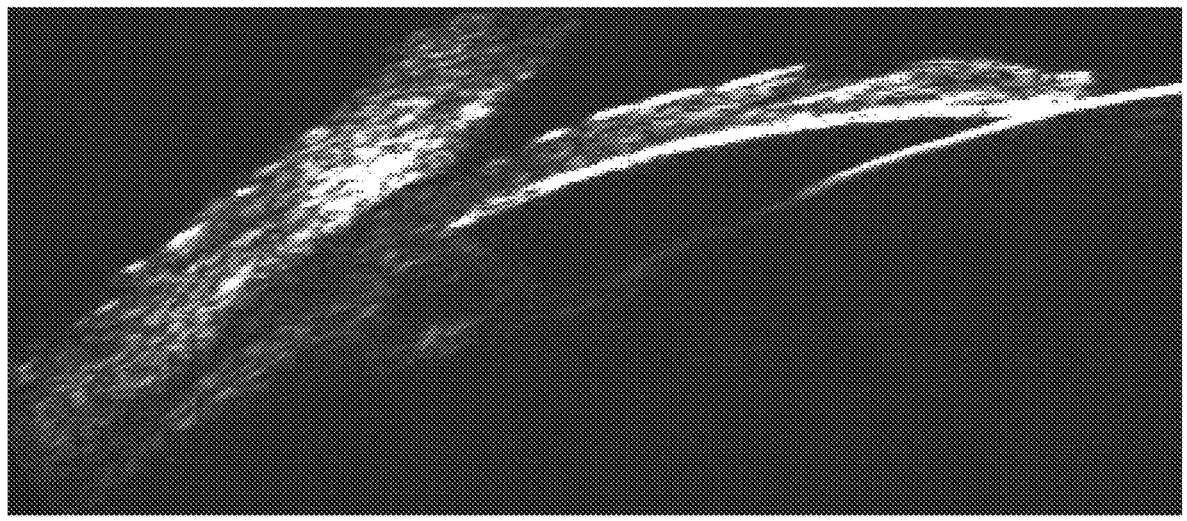
FIG. 24A illustrates the interface line between the sclera and ciliary muscles.
Figure 24B:
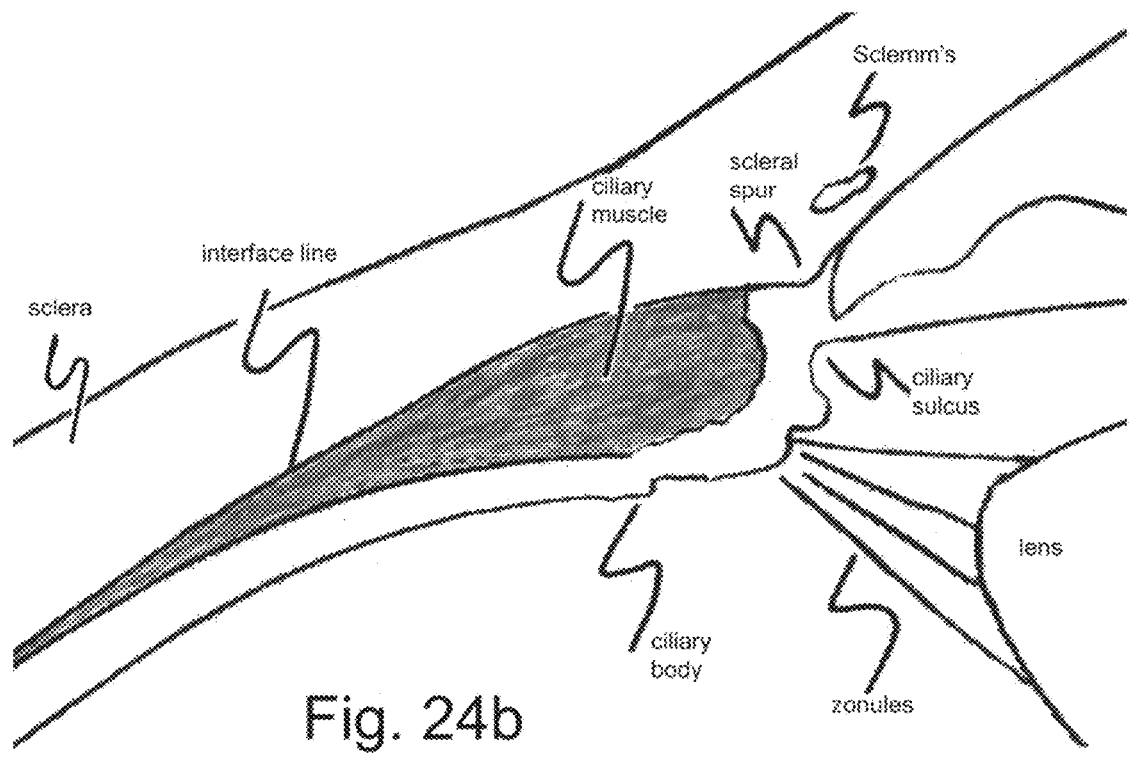
FIG. 24B is a diagram of the anatomy of the eye.

FIG. 24A further illustrates the interface line between the sclera and ciliary muscles. FIG. 24*a* is a B-scan of the region and FIG. 24*b* is a line drawing showing the various features of interest. The interface line as shown in FIG. 24*a* is shown as a boundary between the lighter sclera and the darker ciliary muscle.

The methods of locating the scleral spur used herein include:

1. Method 1 referred to as the Ciliary Muscle method (CM method)
2. Method 2 referred to as the first variation of the Bump method (BM1 method)
3. Method 3 referred to as the second variation of the Bump method (BM2 method)
4. Method 4 referred to as the third variation of the Bump method (BM3 method)

There is also another method known as the Schwalbe Line Method but it is not used in this disclosure.

A general description of these methods can be found in "The Effect of Scleral Spur Identification Methods on Structural Measurements by Anterior Segment Optical Coherence Tomography" Seager, Wang, Arora, Quigley, Journal of Glaucoma, Vol. 23, No 1, January 2014, which is incorporated herein by reference.

14. Now look for the scleral spur on the binarized isolated sclera object

Method 1: the Ciliary Muscle method comprises projecting the curve formed by the interface between the sclera and ciliary muscle (referred to herein as the interface curve—see FIG. 24A) to where it intersects the curve formed by the posterior of the cornea (also known as the Schwalbe Line). The scleral spur is at the intersection of these two curves. To find this intersection point, determine the local slope (computed as a moving average) along the interface curve between the lighter sclera and the darker ciliary muscle and, while moving toward the iris (left to right as shown in FIG. 1), find the minimum slope or apex of the bump (the inflection point where the slope changes from decreasing to increasing). Identify this point as a possible first scleral spur.

The local slope is computed as a moving average because of the unevenness of the interface curve on the scale of the resolution of a precision arc scanning device (about 25 microns range resolution and about 40 microns lateral resolution).

Method 2: starting at a point on the interface curve about 1 mm to the left of the first scleral spur found by Method 1, form a line from this point to a point on the Schwalbe curve about 1 mm to the right of the scleral spur found by Method 1. Call this the first "scleral slope line". Slide a perpendicular to this scleral slope line along the scleral slope line. For each perpendicular, measure the distance from the first scleral slope line to the interface curve. The maximum distance recorded will be the apex of the bump. Identify this point as a possible second scleral spur.

Method 3: determine a second scleral slope line by starting at a point on the interface curve about 2 mm to the left of the first scleral spur found by Method 1, form a line from this point to the rightmost point used in Method 1. Call this the second "scleral slope line". Slide a perpendicular to this second scleral slope line along the second scleral slope line. For each perpendicular, measure the distance from the second scleral slope line to the interface curve. The maximum distance recorded will be the apex of the bump. Identify this point as a possible third scleral spur.

Method 4: starting with a horizontal line anchored at the leftmost point used in Method 3, rotate this horizontal line about this left most point in a counterclockwise direction until it intersects the posterior side of the interface curve between the sclera and ciliary muscle and identify that point as a possible fourth scleral spur.

Schwalbe's line is formed by the posterior surface of the eye's cornea. The Schwalbe Line Method was not used in the method described in this disclosure.

15. Determine the best prediction of the scleral spur location by comparing the locations of the potential spurs determined using the four methods above, considering proximity to each other, and proximity to the iris root. Calculate a score or confidence factor based on those factors.

Figure 19A:
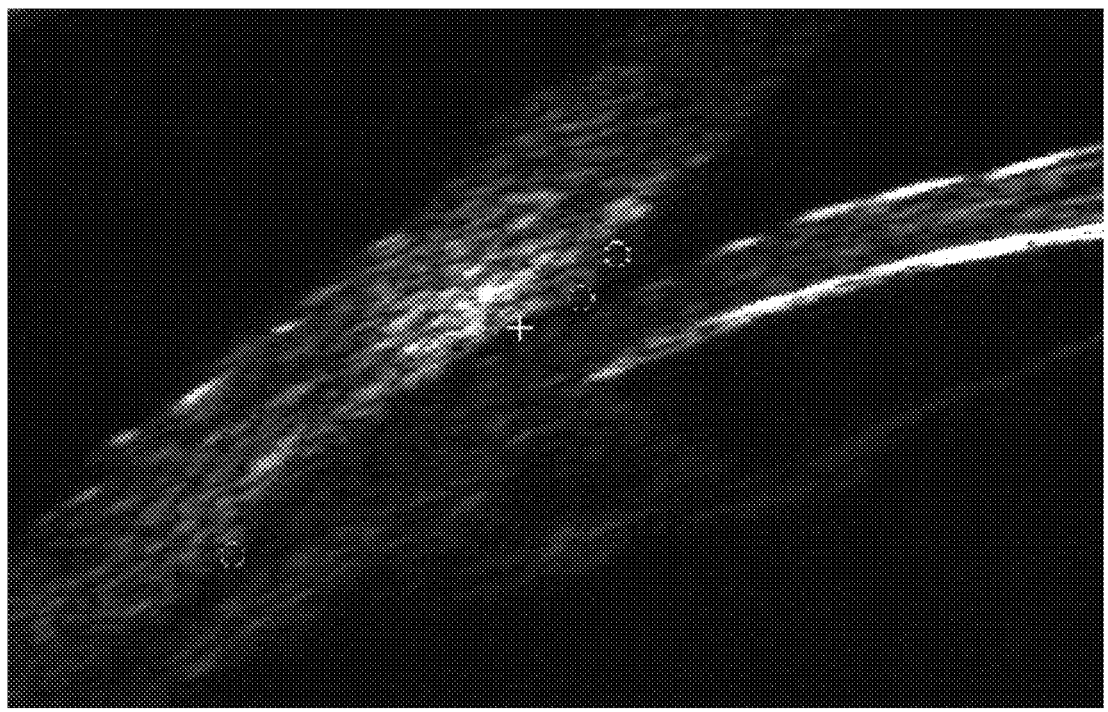
FIG. 19A shows the point of intersection of the iris root and sclera, along with potential points of the scleral spur detected with a longer isolated sclera.
Figure 19B:
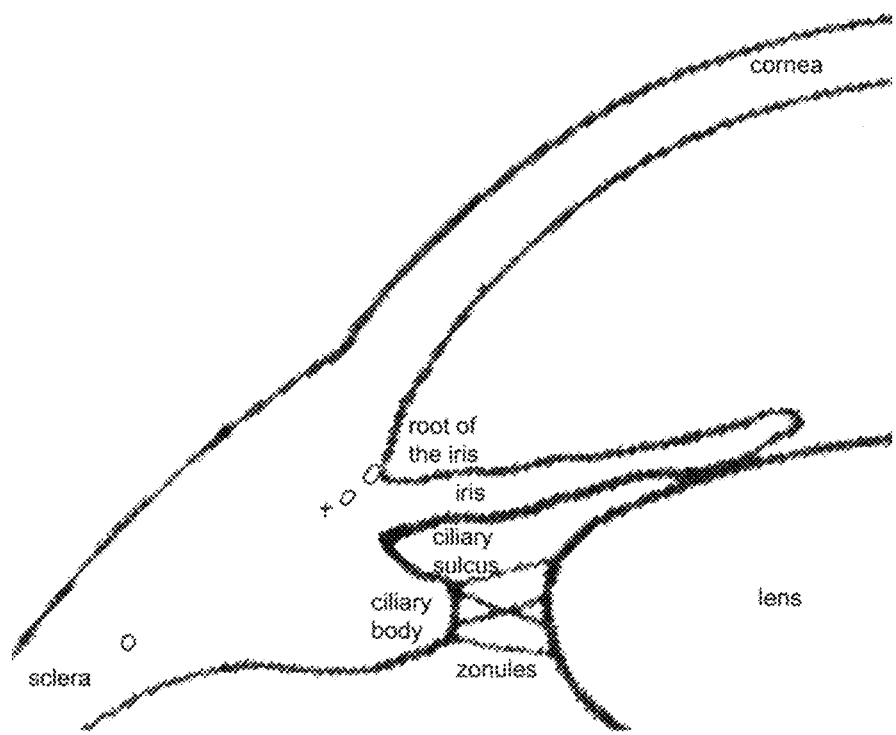
FIG. 19B is a diagram of the anatomy of the eye.
Figure 20:
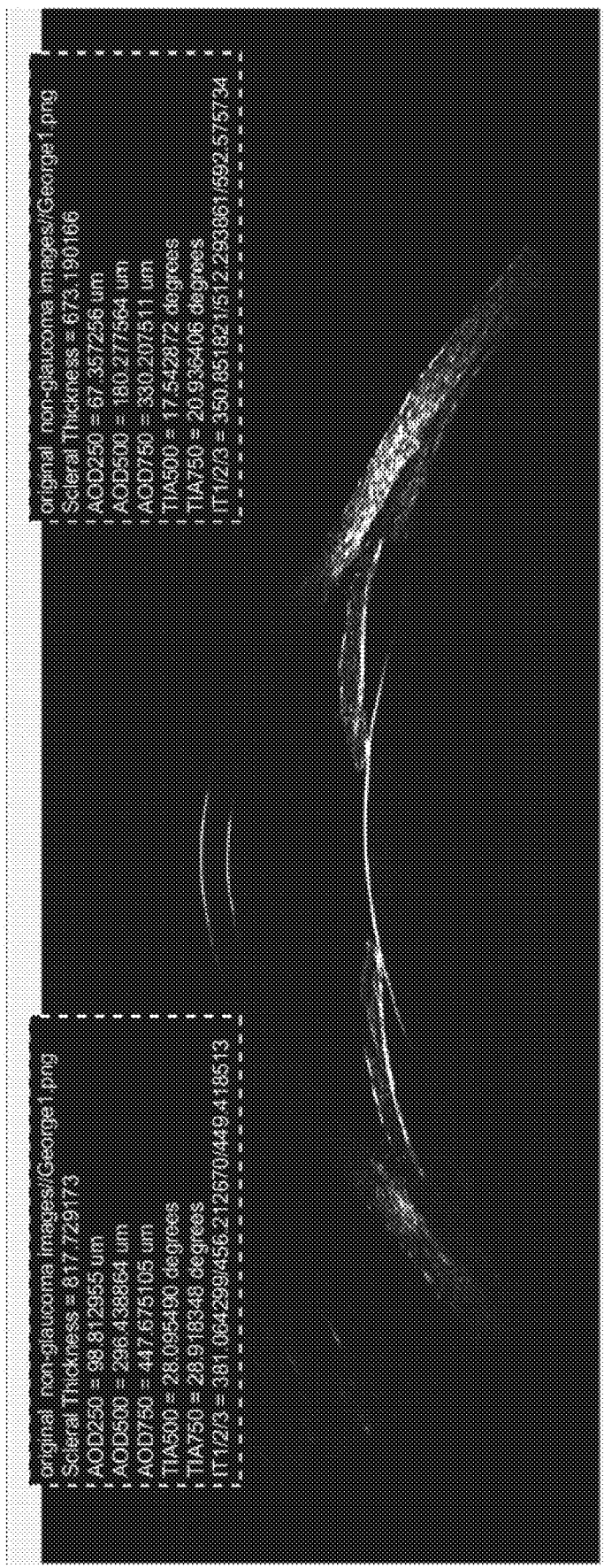
FIG. 20 is a B-scan of the anterior segment showing the location of measured features of the left and right eye along with the tables of actual measurements.

16. Repeat steps 17-23 using a shortened ROI. Compare the confidence factors of spurs found by both the shortened sclera and the longer one and use the point with the best confidence factor. The results of locating the potential scleral spurs are illustrated in FIGS. 19A and 20. Examples of a final determination of the location of the spurs can be seen in FIGS. 12A, 13, and 18A.

Determine Measurements Referenced to the Scleral Spur and or Sulcus Points

FIG. 12A is a B-scan of half of the anterior segment showing the location of features to be measured.

Figure 13:
FIG. 13 is a B-scan of the whole anterior segment showing the location of features to be measured.

FIG. 13 is a B-scan of the whole anterior segment showing the location of features to be measured.

Figure 14:
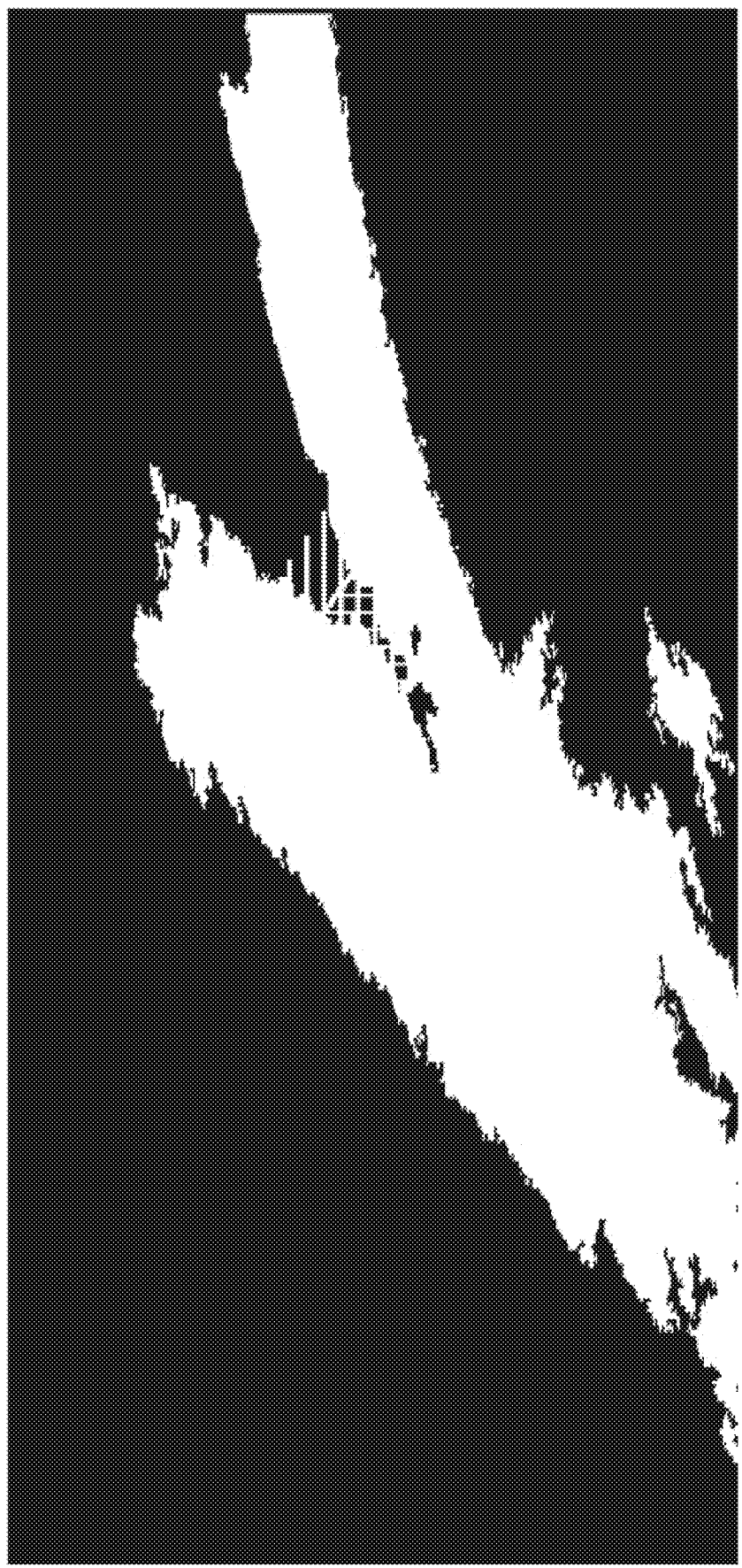
FIG. 14 shows a binarized smoothed image of the scleral region of interest with cross hatching to indicate the TISA areas.

FIG. 14 shows a binarized smoothed image of the scleral region of interest with cross hatching to indicate the TISA areas.

Figure 15A:
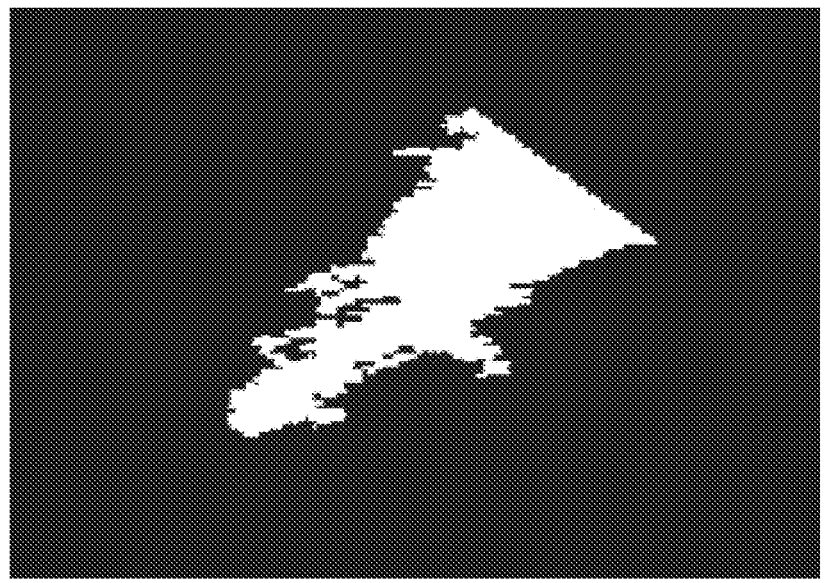
FIG. 15A shows the inverted binarized TISA area object used for measuring the TISA area.
Figure 15B:
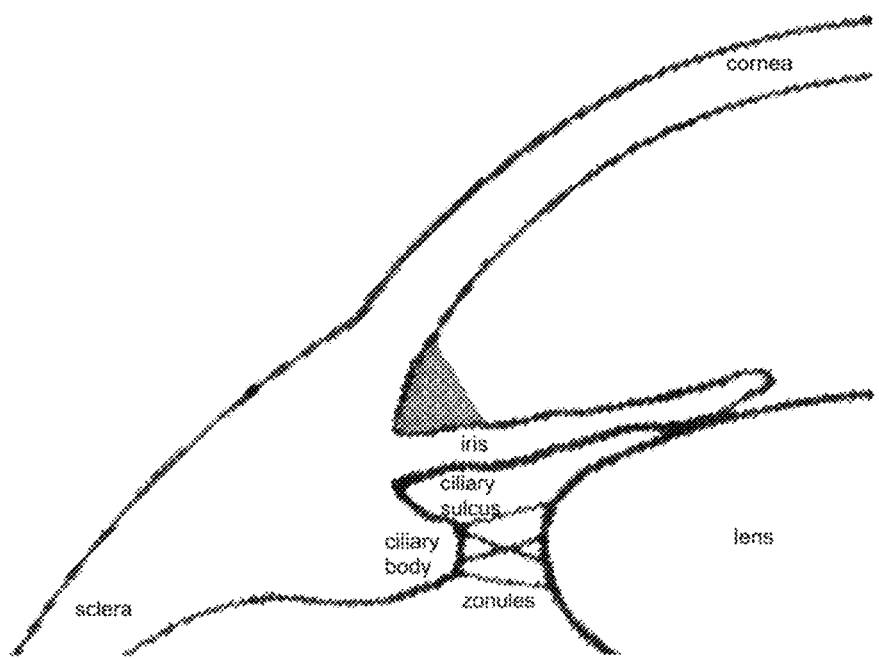
FIG. 15B is a diagram of the anatomy of the eye.

FIG. 15A shows the inverted binarized TISA area object used for measuring the TISA area.

Figure 16:
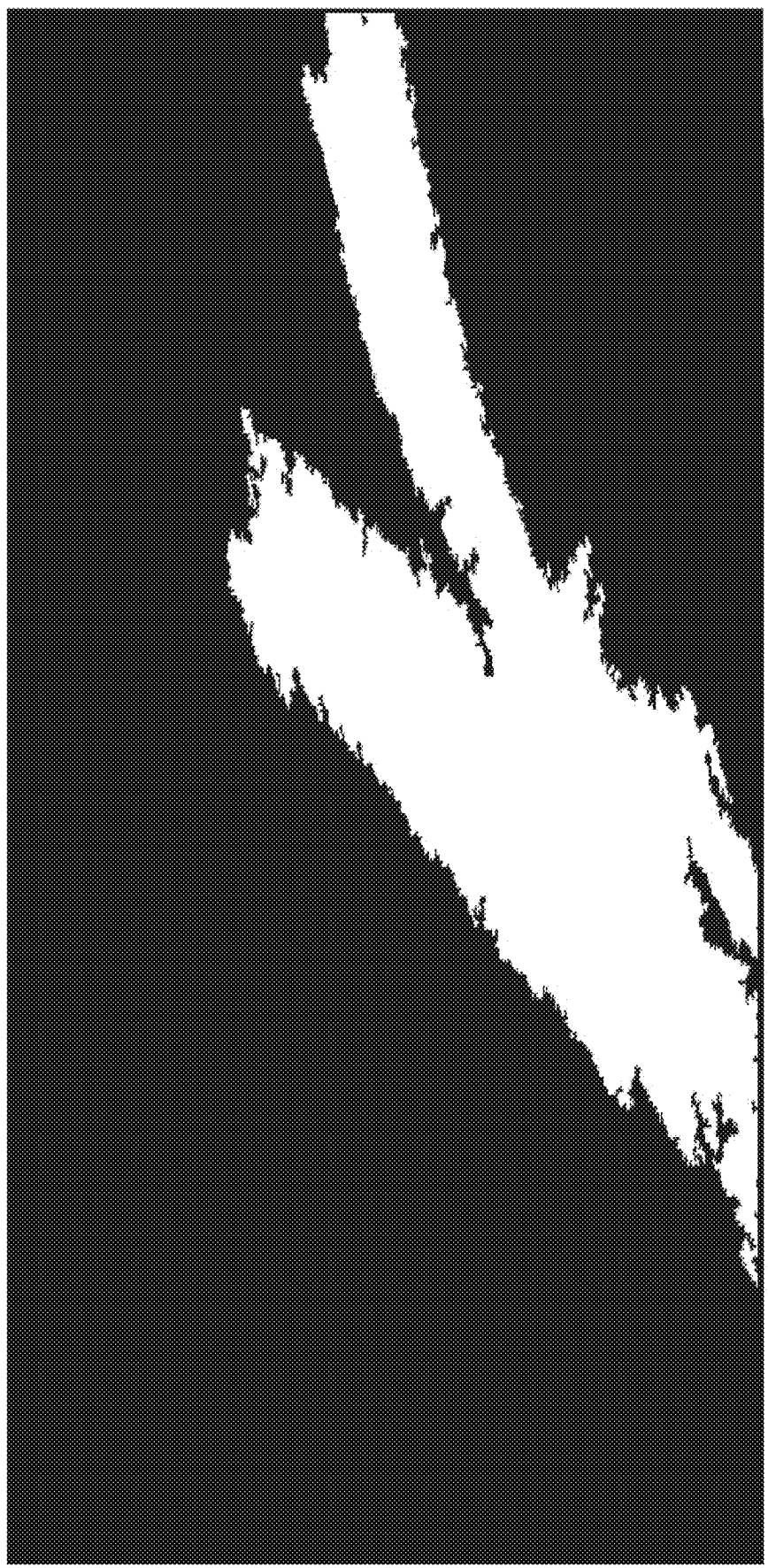
FIG. 16 shows the binarized region of interest for isolating the root of the iris.

FIG. 16 shows the binarized region of interest for isolating the root of the iris.

Figure 17:
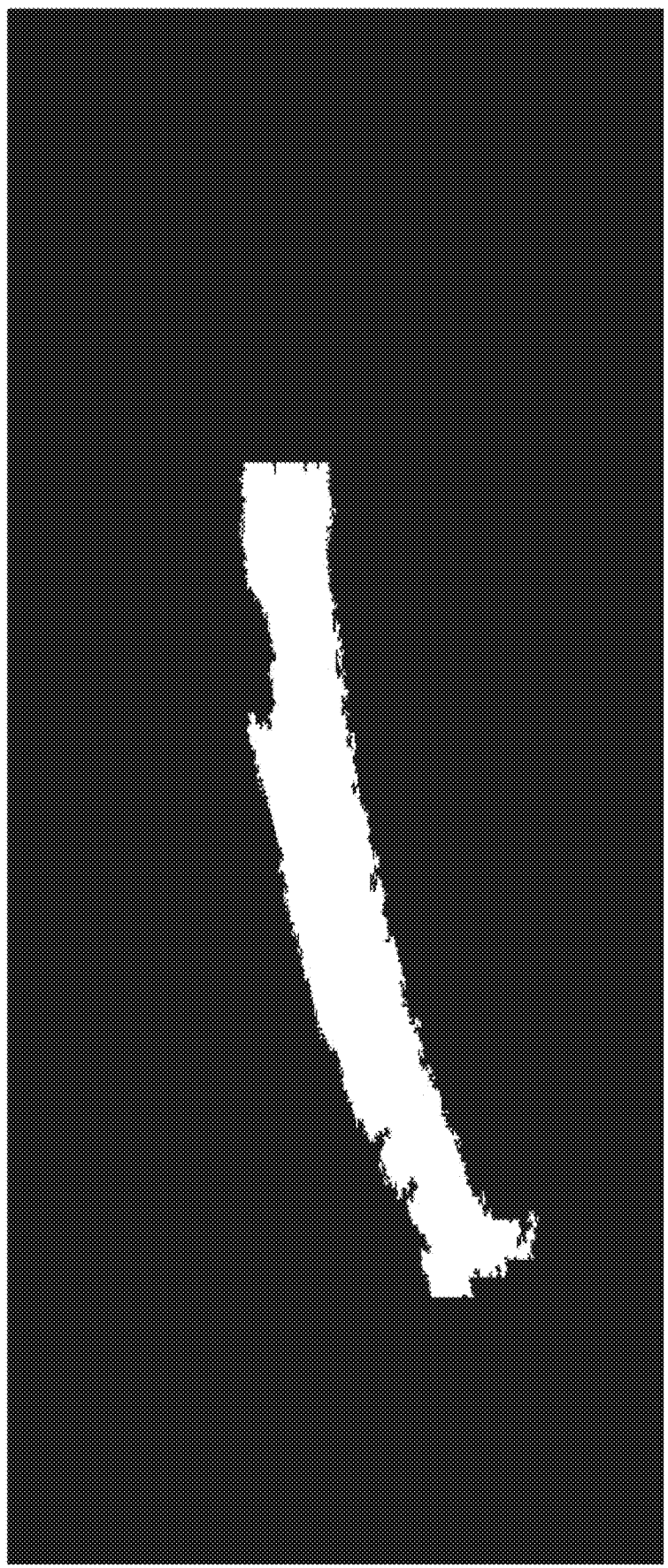
FIG. 17 shows the binarized image of the isolated iris.

FIG. 17 shows the binarized image of the isolated iris.

Figure 18A:
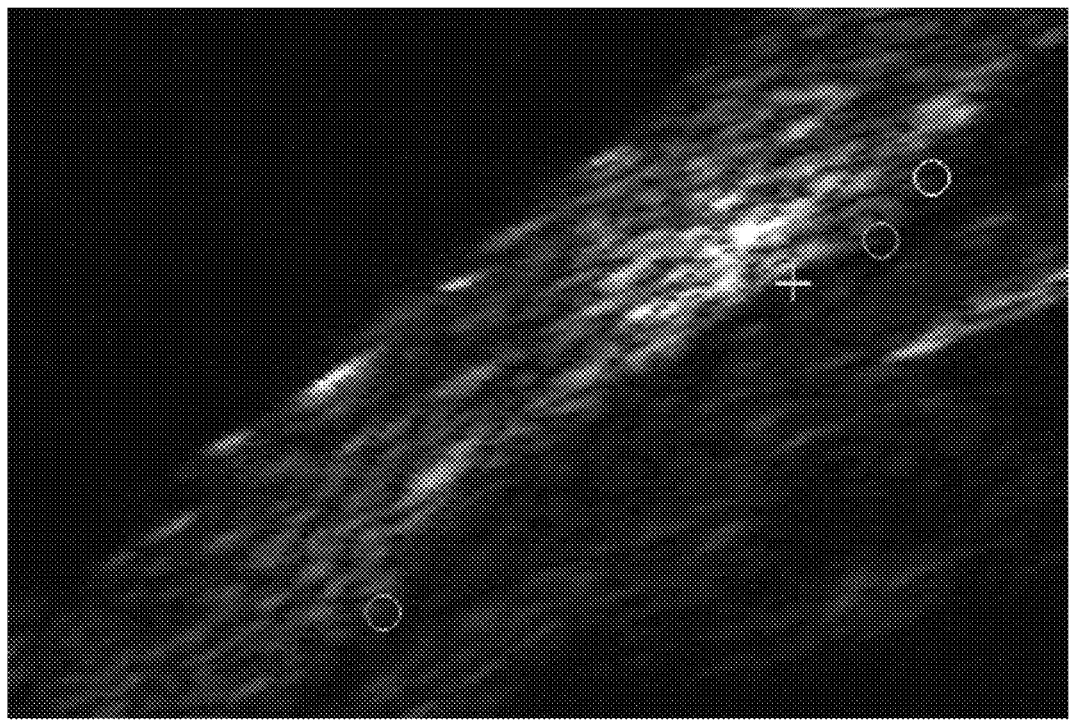
FIG. 18A shows the point of intersection of the iris root and sclera, along with potential points of the scleral spur detected with shortened isolated sclera object.
Figure 18B:
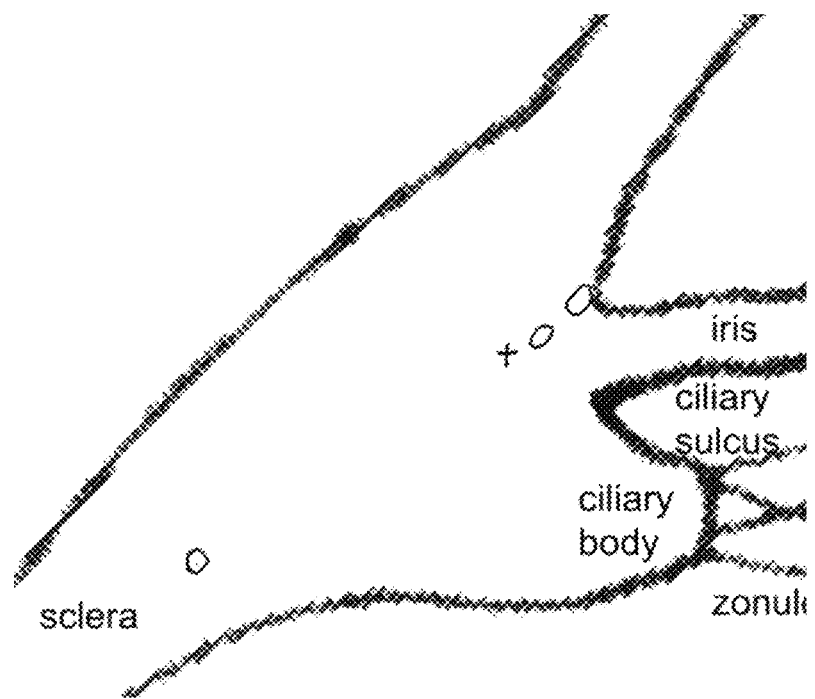
FIG. 18B is a diagram of the anatomy of the eye.

FIG. 18A shows the point of intersection of the iris root and sclera, along with potential points of the scleral spur detected with shortened isolated sclera object.

FIG. 19A shows the point of intersection of the iris root and sclera, along with potential points of the scleral spur detected with a longer isolated sclera.

FIG. 25A illustrates various measurements that can be made using ultrasound technology. FIG. 25a illustrates the iridocorneal angle or simply "angle". FIG. 25b shows the other measurements which are made with reference to the location of the scleral spur. The measurements of ICPD, IZD, ILCD, ID1, ID2 and ID3 all require ultrasound technology to be imaged and require precision ultrasound technology to be measured with accuracy and reproducibility.

Figure 21:
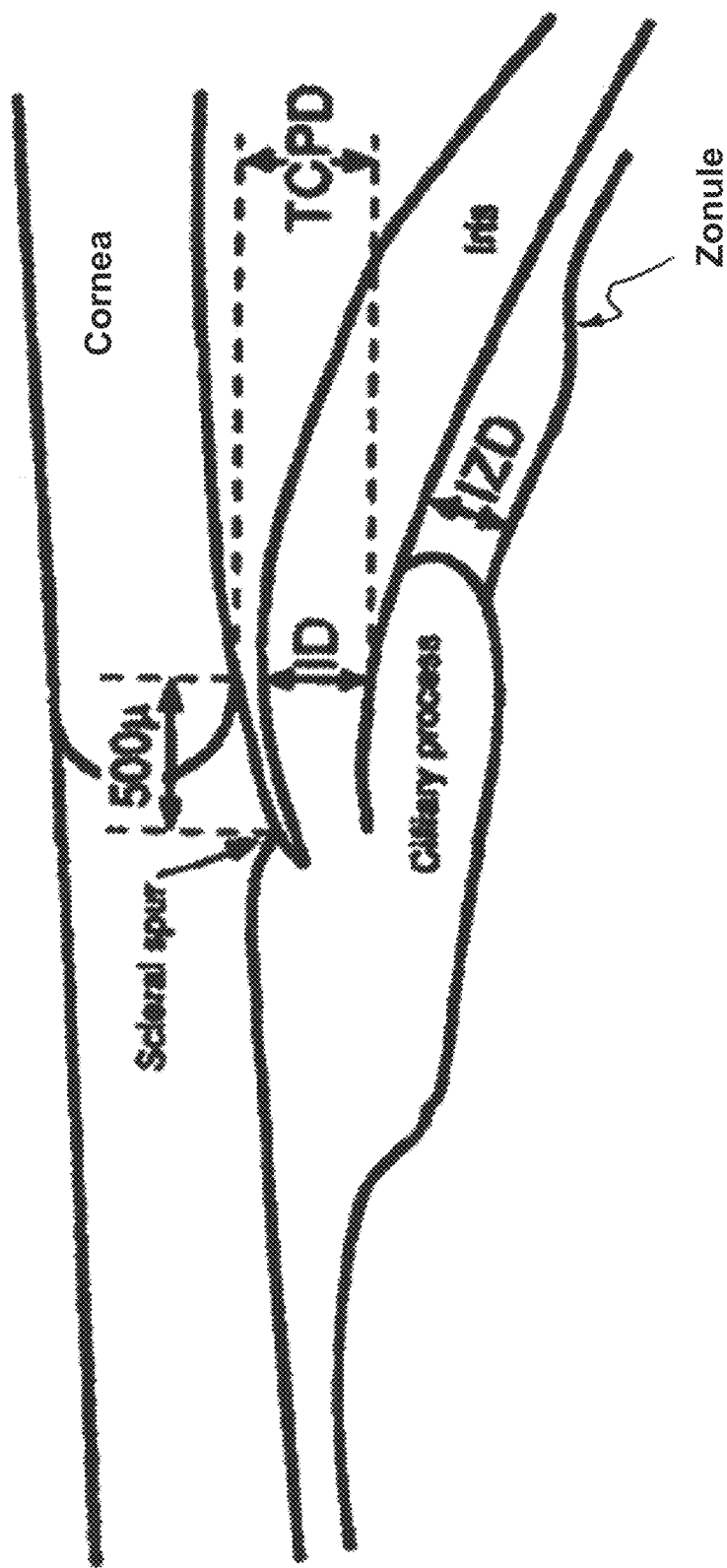
FIG. 21 illustrates another measurement of the iris zonule distance IZD. This measurement is also made through the iris.

FIG. 21 illustrates another measurement of the iris zonule distance IZD.

17. Once the scleral spur has been located, then the other measurements can be made. These are:

a. Scleral Thickness (ST) is the thickness from the scleral spur to the anterior surface of the sclera, along a line perpendicular to anterior surface of the sclera.

b. Angle-opening distance AODn μm is the distance from cornea to iris at nμm from the scleral spur, along the scleral wall (n typically=250, 500 and 750)

c. Trabecular-iris contact length TICL μm is the linear distance of contact between iris and cornea/sclera beginning at scleral spur d. Angle-recess area ARAn μm2 is the area of triangle between angle recess and iris and cornea nμm from scleral spur (n typically 250, 500 and 750)

e. Trabecular-iris space TISA μm2 is the area of trapezoid between iris and cornea from sclera to nμm (n typically 250, 500 and 750). Images showing the TISA are illustrated in FIGS. 14 and 15A.

f. Trabecular-iris angle TIA Degrees is the angle formed from angle recess to points 500 μm from scleral spur on trabecular meshwork and perpendicular on surface of iris g. Trabecular-ciliary process distance TCPD μm is measured from point on endothelium 500 μm from scleral spur through iris to ciliary process (not implemented yet, but on our radar)

h. Iris-zonular distance IZD μm is the distance from posterior iris surface to first visible zonule at point closest to ciliary body (not implemented yet, but on our radar)

i. Iris Thickness (IT) is the thickness of the iris. The IT500 thickness is measured along a line perpendicular to the iris axis that intersects the AOD500 point along the sclera. The IT2 mm thickness is measured with a line parallel to the IT500 line, 2 mm from the iris root, and the IT3 thickness is measured with lines parallel to the IT500 line at the thickest point of the iris. The iris thickness is determined by creating a binarized region of interest including the iris (illustrated in FIGS. 12A and 20), isolating the iris object by increasing the threshold (illustrated in FIG. 17), and making the measurements based on the previously found scleral spur and AOD500 point.

j. Scleral spur-iris insertion distance SS-IR is the linear distance from scleral spur to iris insertion k. Iris radius of curvature IRC mm is the radius of posterior iris surface using an arc transecting three points: iris root, pupil margin and point of maximal iris displacement l. Iris convexity IC mm is the maximum distance from the posterior surface of the iris to the line from posterior iris at pupillary margin to the iris root m. Iris-lens contact distance ILCD mm is the length of contact between surfaces of lens and iris n. Anterior-posterior chamber depth ACD/PCD is the ratio of anterior chamber to posterior chamber depth measured 1 mm from the scleral spur.

Prepare an Automated Report

18. Some of the measurements described above are shown in FIGS. 13, 14, and 22 on a typical output report format with the original B-scan as a background is shown in FIG. 20.

Based on the paper "Ultrasound Biomicroscopy in Plateau Iris Syndrome" by Pavlin, Ritch and Foster, which is incorporated herein by reference, another measurement called the iris to zonule distance (IZD) may also be made by the methods described in the present disclosure. The IZD measurement is illustrated in FIG. 21.

FIG. 22 illustrates geometric structures used in detecting the scleral spur. The curve 2210 formed by the interface between the lighter sclera 2204 and darker ciliary muscle 2209 is referred to herein as the "interface curve". The protruding structure 2208 located at the intersection of the interface curve 2210 and the curve formed by the posterior of the cornea 2201 is referred to herein as "the bump". FIG. 22 also shows the natural lens 2203 and the zonules 2206 that attach lens 2203 to the ciliary body 2205. Also shown is Schlemm's canal 2207 and the ciliary sulcus 2211 formed at the junction of the ciliary body 2205 and the iris 2202.

FIG. 23 is a close-up of geometric structures used in detecting the scleral spur. The curve 2310 formed by the interface between the lighter sclera 2304 and darker ciliary muscle 2309 is interface curve. The protruding structure 2308 located at the intersection of the interface curve 2210 and the curve formed by the posterior of the cornea 2301 is referred to herein as "the bump". FIG. 23 also shows the zonules 2306 that attach lens to the ciliary body 2305. Also shown is Schlemm's canal 2307 and the ciliary sulcus 2311 formed at the junction of the ciliary body 2305 and the iris.

A number of variations and modifications of the inventions can be used. As will be appreciated, it would be possible to provide for some features of the inventions without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. A method for detecting a scleral spur in an eye of a patient, comprising:
providing an ultrasound device having (i) a scan head with an arcuate guide track and a carriage movable along the arcuate guide track; (ii) an eyepiece configured to maintain the eye of the patient in a fixed location with respect to the arcuate guide track; and (iii) a transducer connected to the carriage;
emitting, from the transducer, ultrasound pulses as the carriage moves along the arcuate guide track;
storing received ultrasound pulses on a non-transitory computer readable medium;
forming, by at least one electronic device, a B-Scan of the eye of the patient based on the received ultrasound pulses;
binarizing, by the at least one electronic device, the B-Scan from a grayscale color palette to a black/white color palette;
determining, by the at least one electronic device, an average surface of a sclera of the eye; and
locating, by the at least one electronic device, a bump of the average surface of the sclera that corresponds to a scleral spur.

2. The method of claim 1, further comprising:
smoothing, by the at least one electronic device, the average surface of the sclera by deleting discrete areas on both sides of the average surface.

3. The method of claim 2, further comprising:
locating, by the at least one electronic device, the bump of the average surface of the sclera by identifying an inflection point of a slope of a posterior side of a pigment epithelium of a pupil dilator muscle.

4. The method of claim 1, further comprising:
determining, by the at least one electronic device, an angle-opening distance from a cornea to an iris of the eye at a predetermined distance from the scleral spur.

5. The method of claim 1, further comprising:
beginning on a left side of a region of interest and moving right until a black discrete area;
inverting, by the at least one electronic device, the black/white color palette; and
locating, by the at least one electronic device, a leftmost white discrete area, which corresponds to a point of interest.

6. The method of claim 5, wherein the point of interest is at least one of a root of an iris of the eye or a root of a ciliary sulcus of the eye.

7. The method of claim 1, further comprising:
determining, by the at least one electronic device, an iris-lens contact distance between a surface of an iris of the eye and a surface of a lens of the eye.

8. A system for detecting a scleral spur in an eye of a patient, comprising:
an ultrasound device, having:
a scan head comprising an arcuate guide track and a carriage movable along the arcuate guide track;
an eyepiece configured to maintain the eye of the patient in a fixed location with respect to the arcuate guide track;
a transducer connected to the carriage, wherein ultrasound pulses are emitted into the eye of the patient, and received ultrasound pulses are stored on a non-transitory computer readable medium; and
at least one electronic device comprising the non-transitory computer readable medium, the non-transitory computer readable medium comprising instructions that, when executed, cause the at least one electronic device to:
form a B-Scan of the eye of the patient based on the received ultrasound pulses;
binarize the B-Scan from a grayscale color palette to a black/white color palette;

determine an average surface of a sclera of the eye; and
locate a bump of the average surface of the sclera that corresponds to the scleral spur.

9. The system of claim 8, further comprising:
instructions that, when executed, cause the at least one electronic device to: smooth the average surface of the sclera by deleting discrete areas on both sides of the average surface.

10. The system of claim 9, further comprising:
instructions that, when executed, cause the at least one electronic device to:
locate the bump of the average surface of the sclera by identifying an inflection point of a slope of a posterior side of a pigment epithelium of a pupil dilator muscle.

11. The system of claim 8, further comprising:
instructions that, when executed, cause the at least one electronic device to:
determine an angle-opening distance from a cornea to an iris of the eye at a predetermined distance from the scleral spur.

12. The system of claim 8, further comprising:
instructions that, when executed, cause the at least one electronic device to:
begin on a left side of a region of interest and move right until a black discrete area;
invert the black/white color palette; and
locate a leftmost white discrete area, which corresponds to a point of interest.

13. The system of claim 12, wherein the point of interest is at least one of a root of an iris of the eye or a root of a ciliary sulcus of the eye.

14. The system of claim 12, further comprising:
instructions that, when executed, cause the at least one electronic device to:
determine an iris-lens contact distance between a surface of an iris of the eye and a surface of a lens of the eye.

15. A system for binarizing a B-Scan of an eye of a patient, comprising:
an ultrasound device, having:
a scan head comprising an arcuate guide track and a carriage movable along the arcuate guide track;
an eyepiece configured to maintain the eye of the patient in a fixed location with respect to the arcuate guide track;
a transducer connected to the carriage, wherein ultrasound pulses are emitted into the eye of the patient, and received ultrasound pulses are stored on a non-transitory computer readable medium; and
at least one electronic device comprising the non-transitory readable medium, the non-transitory computer readable medium comprising and having instructions that, when executed, cause the at least one electronic device to:
form a B-Scan of the eye of the patient based on the received ultrasound pulses;
determine an average intensity of a grayscale color palette of the B-Scan of the eye; and
binarize the B-Scan of the eye from the grayscale color palette to a black/white color palette, wherein discrete areas of the B-Scan above a predetermined intensity are binarized to white and discrete areas of the B-Scan below the predetermined intensity are binarized to black, and the predetermined intensity depends on the average intensity.

16. The system of claim 15, wherein the predetermined intensity is greater than the average intensity.

17. The system of claim 15, further comprising:
instructions that, when executed, cause the at least one electronic device to:
determine an average surface of a sclera of the eye; and
locate a bump of the average surface of the sclera that corresponds to a scleral spur.

18. The system of claim 15, where a discrete area is a pixel and the B-Scan is a rasterized image.

19. The system of claim 17, further comprising:
instructions that, when executed, cause the at least one electronic device to:
smooth the average surface of the sclera by deleting discrete areas on both sides of the average surface.

20. The system of claim 19, further comprising:
instructions that, when executed, cause the at least one electronic device to:
locate the bump of the average surface of the sclera by identifying an inflection point of a slope of a posterior side of a pigment epithelium of a pupil dilator muscle.

* * * * *